United States Patent [19]
Wodicka et al.

[11] Patent Number: 5,445,144
[45] Date of Patent: Aug. 29, 1995

[54] APPARATUS AND METHOD FOR ACOUSTICALLY GUIDING, POSITIONING, AND MONITORING A TUBE WITHIN A BODY

[75] Inventors: George R. Wodicka, West Lafayette; Jeffrey P. Mansfield, Lafayette; William D. Voorhees, West Lafayette, all of Ind.

[73] Assignee: Purdue Research Foundation, West Lafayette, Ind.

[21] Appl. No.: 168,992

[22] Filed: Dec. 16, 1993

[51] Int. Cl.⁶ ............................................. A61M 16/00
[52] U.S. Cl. .............................. 128/207.14; 128/656; 128/899
[58] Field of Search .............................. 128/897–899, 128/715, 656–658, 207.14

[56] References Cited

U.S. PATENT DOCUMENTS

| | | |
|---|---|---|
| 3,938,502 | 2/1976 | Bom . |
| 4,155,356 | 5/1979 | Venegas . |
| 4,326,416 | 4/1982 | Fredberg . |
| 4,567,882 | 2/1986 | Heller . |
| 4,757,821 | 7/1988 | Snyder . |
| 4,949,716 | 8/1990 | Chenoweth . |
| 4,951,678 | 8/1990 | Joseph et al. . |
| 5,081,993 | 1/1992 | Kitney et al. . |
| 5,085,221 | 2/1992 | Ingebrigtsen et al. . |
| 5,099,845 | 3/1992 | Besz et al. ............... 128/899 X |
| 5,316,024 | 5/1994 | Hirschi et al. ............ 128/903 X |

FOREIGN PATENT DOCUMENTS

| | | |
|---|---|---|
| 0046987 | 3/1982 | European Pat. Off. . |
| 0284055 | 9/1988 | European Pat. Off. . |
| 2068735 | 8/1981 | United Kingdom . |
| 2102127 | 1/1983 | United Kingdom ............ 128/899 |
| 129788 | 5/1959 | U.S.S.R. . |
| 214014 | 6/1968 | U.S.S.R. . |
| 309699 | 9/1971 | U.S.S.R. . |
| 401351 | 2/1974 | U.S.S.R. . |
| 459234 | 3/1975 | U.S.S.R. . |

OTHER PUBLICATIONS

Raphael et al., "Ultrasound Confirmation of Endotracheal Tube Placement", J Clin Ultrasound, vol. 15, pp. 459–462, Sept. 1987.

Lingle, "Sonographic Verification of Endotracheal Tube Position in Neonates: A Modified Technique", J Clin Ultrasound, vol. 16(8), pp. 605–608, Oct. 1988.

Slovis et al., "Endotracheal Tubes in Neonates: Sonographic Positioning", Radiology, vol. 160, pp. 262–263, 1986.

Jackson, "Airway Geometry by Analysis of Acoustic Pulse Response Measurements", J. Appl. Physiol., pp. 523–536, 1977.

Fredberg, "Airway Area by Acoustic Reflections Measured at the Mouth", American Physiological Society, 1980.

Wodicka et al., "A Model of Acoustic Transmission in the Respiratory System", IEEE Trans. Biomed. Eng. 36: pp. 925–934, 1989.

Wodicka et al., "Spectral Characteristics of Sound Transmission in the Human Respiratory System", IEEE Trans. Biomed. Eng. 37: pp. 1130–1135, 1990.

Wodicka et al., "Transfer Function of Sound Transmission in Subglottal Human Respiratory System at Low Frequencies", American Physiological Society, pp. 2126–2130, 1990.

*Primary Examiner*—Angela D. Sykes
*Attorney, Agent, or Firm*—Barnes & Thornburg

[57] ABSTRACT

An apparatus and method is disclosed for acoustically guiding a distal end of a tube within a body. The apparatus and method generates an incident sound pulse in the tube which propagates into the body, detects sound pulses resulting from the incident sound pulse and from reflected sound pulses from within the body, and processes the detected sound pulses to guide insertion of the distal end of the tube within the body. The apparatus and method provides an indication of the position of the distal end of the tube within the body conduit, estimates dimensions of the body conduit adjacent the distal end of the tube, and determines if the tube is obstructed.

25 Claims, 14 Drawing Sheets

APPARATUS AND METHOD FOR ACOUSTICALLY GUIDING, POSITIONING, AND MONITORING A TUBE WITHIN A BODY

BACKGROUND AND SUMMARY OF THE INVENTION

The present invention relates to an apparatus and method for acoustically guiding, positioning, and monitoring a tube or catheter within a body. More particularly, the present invention relates to an apparatus and method to guide the placement a tube in a body conduit or cavity, to monitor the position of the tube, and to insure the patency of the tube in the body using a noninvasive acoustic reflectance technique.

The specific example of placement of an endotracheal tube (hereinafter "ETT") inserted into the airways of a respiratory system is disclosed. However, it is understood that the acoustical guidance apparatus and method of the present invention may be used in connection with guiding other types of tubes, catheters, or similar devices into various body conduits or cavities.

For the case of ETT placement, the structure of the human airways are extremely complex. The ends of the trachea are characterized by the larynx (which contains the vocal folds) cranially and a first bifurcation, known as the carina, caudally. The adult trachea is approximately 1.4 to 1.6 cm in diameter and 9 to 15 cm long. The newborn trachea averages about 0.5 cm in diameter and 4 cm in length. The airways that are formed by the carina are the right primary bronchus and the left primary bronchus. The right primary bronchus is shorter, wider, and more vertical than the left primary bronchus. For this reason a majority of ETT insertions past the carina tend to follow the right primary bronchus. Continuing farther down the airways, the bronchial tubes branch into smaller and smaller tubes. They finally terminate into alveoli, small airfilled sacs where the oxygen-carbon dioxide gas exchange takes place. The lungs consist of approximately $10^7$ airways with 35 branching generations terminated into nearly 300 million alveoli.

An ETT is inserted through the mouth and into the trachea of a patient for several reasons: (1) to establish and maintain an open airway; (2) to permit positive pressure ventilation which cannot be done effectively by mask for more than brief periods; (3) to seal off the digestive tract from the trachea thereby preventing inspiration of forced air into the stomach; and (4) as an anesthesia delivery system. Endotracheal intubation may be complicated by inadvertent insertion of the ETT into the esophagus, or past the carina into one of the right primary bronchus or the left primary bronchus. Improper placement of the ETT into the esophagus is most evident in the emergency room setting characterized by high stress and limited time. Insertion of the ETT past the carina will result in ventilation of only the right or left lung. Also, postplacement movement of the distal ETT tip either past the carina or above the vocal folds due to patient or ventilator tube movement, or mucous blockage of the ETT lumen, can occur over time. In all of these scenarios, the patient is ineffectively ventilated which may result in severe medical complications.

In an attempt to avoid these possible complications, techniques have been developed to aid clinicians in the determination of the location of an ETT. The general guidelines for an ideal method are as follows: (1) the test should work for difficult intubations; (2) positive tests which indicate a proper ETT tip location must be unequivocal; (3) esophageal intubation must always be detected; and (4) clinicians must understand the test. The known techniques for clinical evaluation of ETT location include stethoscopic evaluation of airway, breath, and epigastric sounds, respiratory system compliance measurements, detection of asymmetrical chest excursion, chest compression techniques, palpation of the ETT cuff over the extrathoracic trachea, electromagnetic detection devices, ultrasonic techniques, optical techniques, carbon-dioxide measurements, suctioning devices, and chest x-rays.

Due to various shortcomings, only chest x-rays and carbon-dioxide measurements are used in a widespread clinical manner. The chest x-ray technique suffers from lengthy assessment time, significant cost, and radiation exposure if multiple measurements need to be taken. The carbon-dioxide technique cannot be used to determine the exact position or patency of the ETT in the respiratory tract, or to directly detect bronchial intubation. In other techniques, specialized apparatus and skilled clinicians are required, and accuracy may depend more on the ability and experience of the clinician than the actual technique. In addition, the clinical need remains for an instrument that can continuously monitor ETT position and patency after placement.

Audible sound has been used to determine the location of a suctioning catheter within the airways. See, for example, United Kingdom Patent Document No. 2,068,735 to Kubota. The sound is introduced into the proximal end of the catheter, exits the distal end, and is detected by a stethoscope on the chest wall. The chest wall location of the strongest sound signal is used to determine catheter location. This method does not include a microphone to monitor acoustic reflections from the tube or catheter and has not been used to assure proper positioning of an ETT within the trachea.

Techniques have also been developed that employ audible sound reflections to determine physical characteristics of passageways in living subjects such as the airway from measurements-made at the mouth. See, for example, U.S. Pat. No. 4,326,416 to Fredberg. These techniques have not been used in conjunction with a moveable tube or catheter such as an ETT to guide placement, determine position, or insure patency within the body.

The acoustical properties of the airways of a respiratory system change dramatically over the audible frequency range. At very low frequencies, the large airway walls are yielding and significant wall motion occurs in response to intra-airway sound. In this frequency range, the airways cannot be represented accurately as rigid conduits and their overall response to sonic pulses is predictably complex. At very high audible frequencies, the large airway walls are effectively more rigid due to their inherent mass. However, one-dimensional sound propagation down each airway segment cannot be insured as the sonic wavelengths approach in size the diameter of the segment and effects of airway branching are thought to increase in importance. There appears to be a finite range of frequencies between roughly 500 and 6,000 Hz where the large airways behave as nearly rigid conduits and the acoustical effects of the individual branching segments are not dominant. It is over this limited frequency range where the complicated branching network can be approximately represented as a flanged "horn" and where its composite acoustical properties reflect the total cross-sectional area of the airways.

The present invention advantageously exploits the acoustical properties of the airways and provides a noninvasive instrument to monitor ETT position. Design criteria for the present invention included that the instrument be: 1) able to distinguish between esophageal, tracheal, and bronchial intubations; 2) sensitive to small movements of the tube; 3) able to continuously monitor ETT position over time; 4) noninvasive.

In the present invention, an audible sound pulse is introduced into a wave guide and is recorded as it passes by a microphone located in the wave guide wall. The sonic pulse then enters the connected proximal end of the ETT, propagates down the ETT, and is emitted into the airways. Acoustic reflections occur within the airways and are recorded by the same microphone as they propagate back up the wave guide. A well-defined inverted reflection arises from the point where the total cross-sectional area of the airways increases rapidly, and the difference in timing between the detection of the incident pulse and this reflection is used to determine ETT position or movement. In addition, the amplitude and polarity of a reflection arising from the abrupt change in area between the ETT tip and the airway in which the ETT is placed is used to estimate the cross-sectional area immediately following the ETT distal tip. This information allows discrimination between tracheal and inadvertent bronchial intubation and can be used to insure an adequate fit between ETT and trachea. In the case of an erroneously placed ETT into the esophagus, the well-defined inverted reflection is not observed and the estimated diameter immediately following the ETT tip is erratic and occasionally less than that of the ETT. Mucous fluid deposition within the ETT is detected and quantified by the resulting increased sonic reflections. The instrument has proven extremely reliable in multiple intubation procedures in eight canines and thus noninvasively, reliably, and inexpensively monitors ETT position and patency in a continuous manner.

The characteristics of the reflected pulses that were measured from the airways were similar to that predicted by the aforementioned simple airway model. Four of its key features provide strong support that the airways behave similar to a tube with a flange at its end: the airway reflection's 1) timing corresponded to a boundary roughly 15 to 20 cm below the vocal folds, dependent on canine size, 2) amplitude was inverted as compared to the incident wave indicating an increase in total cross-sectional area A, 3) duration was short (0.7 ms) and 4) energy was a significant fraction (on the average 70%) of that of the incident airway pulse. The last two features indicate that the change in A is large and occurs rapidly from a spatial perspective, as was predicted from the model.

The determinant of the reflection resulting from the change in A between the ETT tip and the airways was confirmed by occluding the ETT on the bench top and observing the reflection polarity change as compared to the unoccluded case. This reflection is extremely useful for three important reasons. Firstly, it provides an index of the appropriateness of fit between the diameter of the ETT and the trachea, and potentially allows the user to optimally match the diameter to the patient via equation (6). ETTs having three different inner diameters of 0.9, 1.0, and 1.1 cm were employed in this study and the procedure of matching ETT size to the animal worked quite well. Secondly, in the case of an erroneous esophageal intubation, it can provide a clear-cut mechanism to discriminate these from proper placement in the trachea through detecting a non-inverted reflection from this boundary owing to a smaller esophageal A as compared to that of the ETT. Since the location of the ETT tip relative to the microphone does not change, it is a simple analytical procedure to assess if this reflection is not inverted and incorporate this information into the guidance system. Lastly, it can be employed to detect movement of the ETT past the carina and into a bronchus, as determined by the decrease in estimated airway cross-sectional $A_{tube}$.

The instrument meets all of the stated design criteria. It is completely noninvasive since it employs audible sound at maximum sound pressure levels of $<120$ dB SPL (re 0.0002 $\mu$bar) which are comparable to those found within the lower vocal tract during normal speech, and are barely audible when connected to the intubated ETT. It is relatively simple in terms of components, requiring a wave guide, speaker, microphone, valve, and signal conditioning/processing hardware. Since measurements can be made either very rapidly or slowly, it can be used to guide placement or monitor changes in ETT position over long periods of time in patients who require extended ventilatory assistance. For these latter cases, ETT patency information is also available. The absolute accuracy of the device to $<0.7$ cm over the insertion length of an entire intubation procedure is adequate to be helpful in clinical situations in adults as well as infants. Also, the differences between the acoustic signals measured for the ETT in the trachea, esophagus, and bronchus provide useful information to guide the placement of the ETT into a proper location for ventilation. Once the ETT tip is placed through the vocal folds and the airway reflection is detected, the ETT can be advanced a preset distance below the vocal folds as guided by the instrument. A "safety zone" can then be defined, with the system indicating through an alarm if the ETT has inadvertently moved outside the zone and that repositioning is required.

According to one aspect of the invention, an apparatus is provided for acoustically guiding a distal end of a tube within a body. The apparatus includes means coupled to the tube for generating an incident sound pulse in the tube which propagates into the body, means for detecting sound pulses in the tube resulting from the incident sound pulse and from reflected sound pulses from within the body, and means for processing the detected sound pulses to guide insertion of the distal end of the tube within the body.

In the illustrated embodiment, the processing means includes means for providing an indication of the position of the distal end of the tube within the body, and means for displaying information generated by the processing means. The apparatus also includes means for monitoring the position of the distal end of the tube within the body. The monitoring means generates a warning signal if the distal end of the tube moves beyond a preset safety zone.

Also in the illustrated embodiment, the processing means includes means for estimating dimensions of the body adjacent the distal end of the tube. The apparatus includes means for generating a warning signal if the dimensions estimated by the estimating means are smaller than dimensions of the distal end of the tube.

The processing means also includes means for determining if the tube is obstructed. The apparatus further includes means for generating a warning signal if the tube is obstructed by more than a predetermined percentage.

Illustratively, the apparatus includes a wave guide having a first end coupled to a proximal end of the tube and a second end, a mechanical ventilator, and a valve movable from a first position to provide communication between the wave guide and the proximal end of the tube to a second position to provide communication between the mechanical ventilator and the proximal end of the tube. The illustrated apparatus further includes comprising an absorptive material coupled to the second end of the wave guide for substantially absorbing sound pulses moving toward the second end of the wave guide.

It is understood that in certain other applications the wave guide may be modified or eliminated. For certain applications, sound pulse generators and detectors may be coupled directly to the tube, either externally or internally.

According to another aspect of the present invention, a method is provided for acoustically guiding a distal end of a tube within a body. The method includes the steps of generating an incident sound pulse in the tube which propagates into the body, detecting sound pulses resulting from the incident sound pulse and from reflected sound pulses from within the body, and processing the detected sound pulses to guide insertion of the distal end of the tube within the body.

In the illustrated method, the processing step includes the steps of providing an indication of the position of the distal end of the tube within the body conduit, estimating dimensions of the body conduit adjacent the distal end of the tube, and determining if the tube is obstructed. The method further includes the steps of monitoring the position of the distal end of the tube within the body, generating a warning signal if the distal end of the tube moves beyond a preset zone, and displaying information generated during the processing step. The method still further includes the steps of generating a warning signal if the dimensions estimated by the estimating means are smaller than dimensions of the distal end of the tube, and generating a warning signal if the tube is obstructed more than a predetermined percentage.

According to a further aspect of the present invention, a method is provided for acoustically guiding a distal end of a tube within a body conduit containing a medium using propagation of sound pulses. The method includes the steps of determining acoustic properties of the medium in the body conduit through which the sound pulses must propagate, determining acoustic properties of a wall of the body conduit, and locating identifiable boundaries within the body conduit which are capable of providing identifiable sound reflections. The method also includes the steps of optimizing characteristics of the sound pulse to provide detectable sound reflections from within the body conduit, generating an incident sound pulse having optimized characteristics in the tube so that the incident sound pulse propagates down the tube and into the body conduit, detecting sound pulses in the tube resulting from the incident sound pulse and from reflected sound pulses from within the body conduit, and processing the detected sound pulses to guide insertion of the distal end of the tube within the body conduit.

Additional objects, features, and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
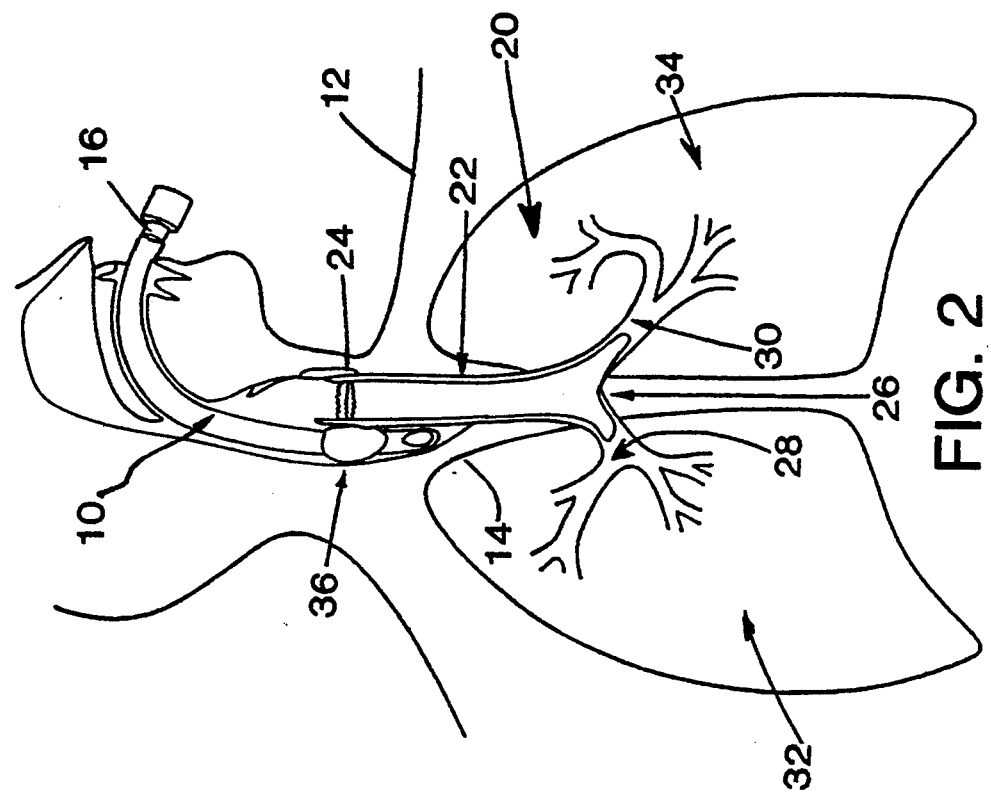
FIG. 1 is a diagrammatical view illustrating proper insertion of an endotracheal tube (ETT) into a trachea of a human body.
Figure 2:
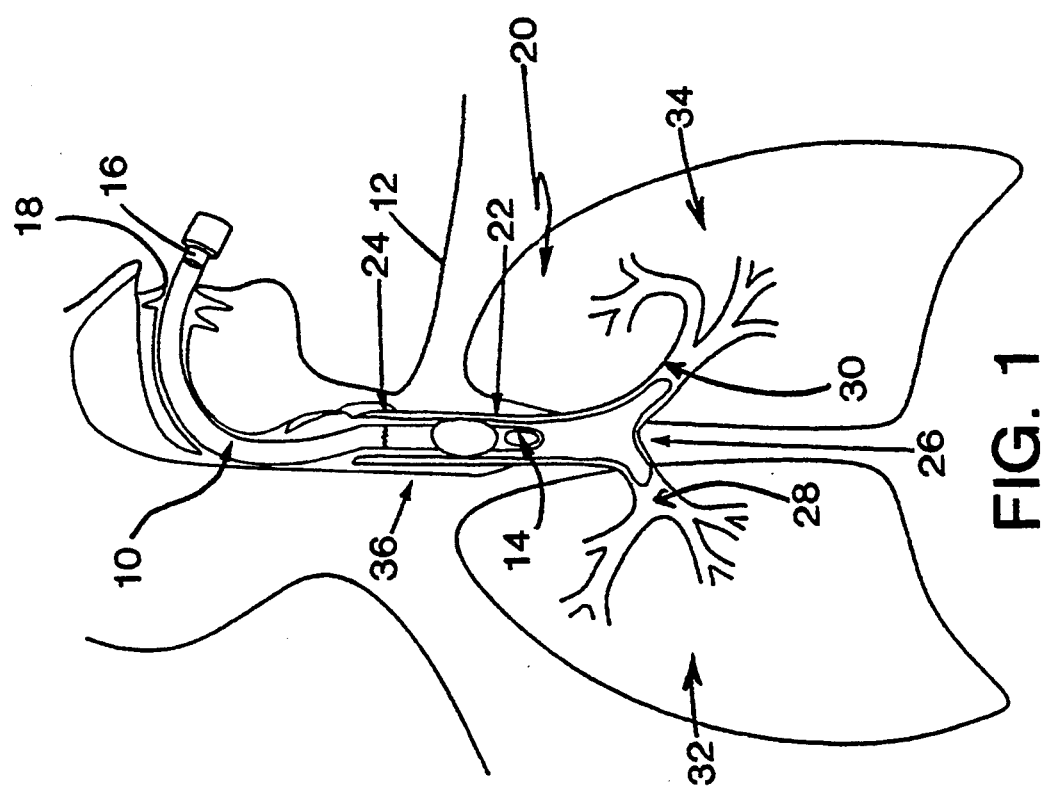
FIG. 2 is a diagrammatical view illustrating improper placement of the ETT into an esophagus.
Figure 3:
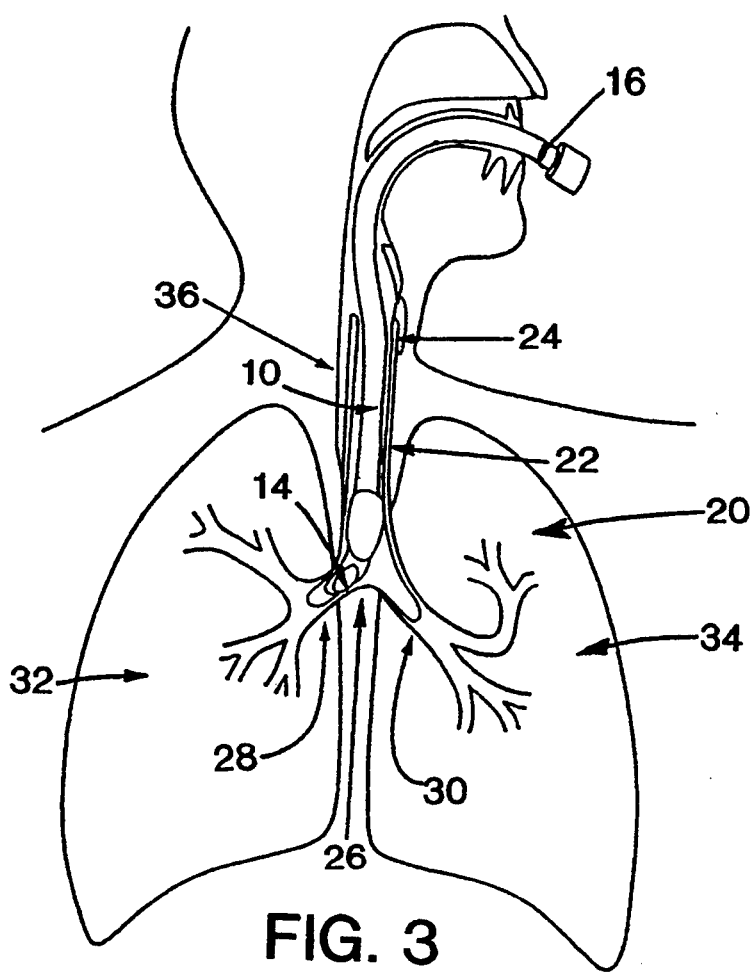
FIG. 3 is a diagrammatical view illustrating improper placement of an ETT past a carina and into a right main bronchus.

Referring now to the drawings, FIGS. 1–3 illustrate insertion of an endotracheal tube (ETT) 10 into a human body 12. ETT 10 includes a hollow tube having a distal end 14 for insertion into body 12 and a proximal end 16 located outside body 12. Illustratively, ETT 10 is inserted into a mouth 18 of the patient. A respiratory system 20 includes a trachea 22 which extends between vocal folds 24 of a larynx and a first bifurcation known as a carina 26. Airways formed by carina 26 include a right primary bronchus 28 and a left primary bronchus 30. Continuing further down the airway, bronchial tubes branch into smaller and smaller tubes.

FIG. 1 illustrates proper insertion of ETT 10 into trachea 22 between vocal folds 24 and carina 26. For proper mechanical ventilation of the patient, it is important that distal end 14 of ETT 10 is positioned properly within trachea 22 between vocal folds 24 and carina 26 to provide adequate ventilation to both lungs 32 and 34. Insertion of ETT 10 into the trachea 22 is sometimes a difficult procedure. As illustrated in FIG. 2, it is possible for distal end 14 of ETT 10 to miss the entrance to trachea 22 and enter an esophagus 36 leading to the stomach (not shown). Improper placement of ETT 10 into esophagus is most evident in an emergency room setting which is characterized by high stress and limited time. Improper placement of open distal end 14 of ETT 10 into the esophagus 36 prevents ventilation of lungs 32 and 34.

Insertion of distal end 14 of ETT 10 past carina 26 will result in ventilation of only right lung 32 or left lung 34. FIG. 3 illustrates improper insertion of distal end 14 of ETT 10 past carina 26 and into right main bronchus 28. Because right primary bronchus 28 is shorter, wider, and more vertical than left primary bronchus 30, the majority of ETT insertions past carina 26 tend to follow the right primary bronchus 28. One object of the present invention is to detect if ETT 10 is improperly inserted into esophagus 36, right primary bronchus 28, or left primary bronchus 30 and alert a user. The apparatus can then be used to guide movement of ETT 10 back into its proper position within trachea 22.

The complex acoustical properties of the airways are determined by their wall properties, branching structure, and cross-sectional area. At the low frequencies associated with breathing, the large airway walls exhibit elastic behavior and alter airway size in response to pressure changes. At higher acoustical frequencies, their behavior is effectively more rigid due to inherent wall mass. The frequency range over which the transition to nearly rigid tube behavior is not known, but for example, modeling and experimental efforts suggest that the trachea approaches rigidity at frequencies near 500 Hz. In contrast to wall properties, the effect of branching on the overall acoustical properties has been hypothesized to be most significant at frequencies above 6,000 Hz as the sonic wavelengths begin to approach airway dimensions. Also, as the sound wavelengths approach airway dimensions with increasing frequency, one-dimensional acoustic wave propagation down the airways cannot be assured as other cross modes of propagation can occur and thereby significantly increase the acoustical complexity of the response.

Thus, there is a band of frequencies between about 500 Hz and about 6,000 Hz over which the acoustical response of the large airways is strongly affected by the cross-sectional area and relatively less affected by wall properties and branching. Over this range it has also been indirectly shown that acoustical losses due to viscous and thermal effects are small. This dictates that plane wave propagation in the large airways at these frequencies would occur at nearly free field speeds as if the airways were rigid conduits. For this mode of propagation, reflections of a sonic pulse occur spatially at points of changes in acoustic impedance $Z$, which equals the characteristic acoustic impedance, $Z_O$:

$$Z = Z_0 = \frac{\rho_0 c}{A} \quad \frac{\text{dyne} \cdot s}{cm^5} \tag{1}$$

where $\rho_0$=density of air in g/cm$^3$, c is the sound speed in cm/s as determined by the density and stiffness of air, and A is the cross-sectional area of the tube in cm$^2$. Thus, for a non-changing propagation medium such as air, Z is predicted to be only a strong function of the cross-sectional area of the tube or airways at frequencies between about 500 Hz and about 6,000 Hz.

Figure 4:
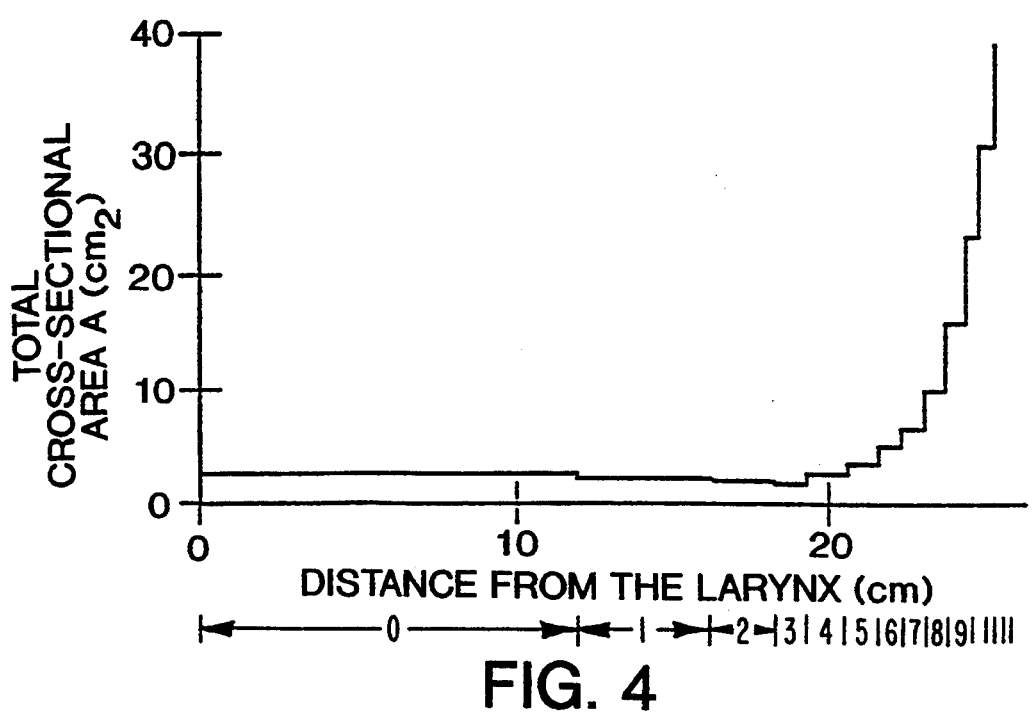
FIG. 4 is a graph representing a total cross sectional area of the airways of a respiratory system versus distance from vocal folds within a larynx.

If one approximates the total cross-sectional area A of the branching airways as a function of the distance below vocal folds 24 as illustrated graphically in FIG. 4, an interesting feature becomes evident. Namely, A is nearly constant for the first few airway branching levels and then increases very rapidly thereafter. This geometrical approximation suggests that from an acoustical perspective, the airways of respiratory system 20 behave in a similar manner to a rapidly flanged "horn" or "trumpet" that is open to a nearly zero-pressure boundary condition at its terminal end.

Figure 5:
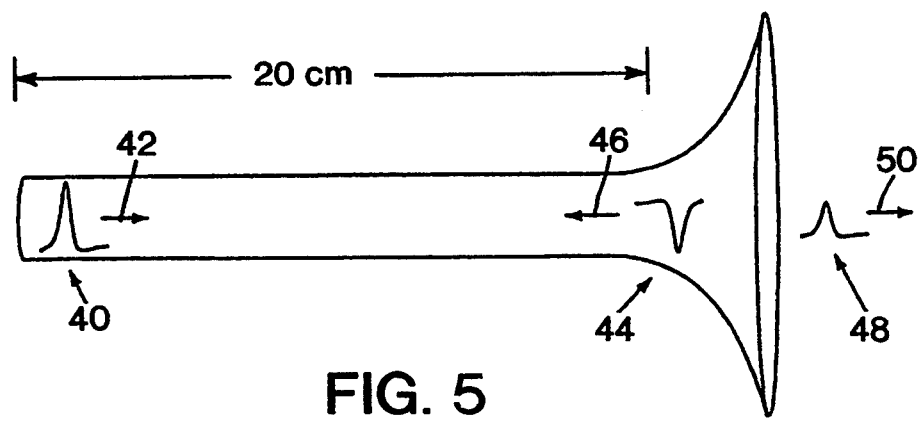
FIG. 5 is a diagrammatical illustration of a simple acoustical flanged "horn" model which represents the acoustical properties of the airway of the respiratory system.

The response of this simple model of the airways to a sound pulse with energy between 500 Hz and 6,000 Hz is depicted in FIG. 5. The incident pulse 40 travels in the direction of arrow 42 in the model without significant reflection for a distance of roughly 20 cm since there is little change in A. When the incident pulse 40 encounters the flared region of the model, a portion 44 of the sonic energy is reflected back up the airways in the direction of arrow 46, and a portion 48 is transmitted further into the branching structure in the direction of arrow 50. Since the flange is quite rapid due to the large spatial rate of change of A, a significant portion of the incident energy is reflected at this "acoustical end" of the airways.

For a plane wave that is incident upon a boundary between two media with acoustic impedances $Z_0$ and $Z_1$, the amplitude of the reflection can be expressed as a dimensionless reflection coefficient, R, equal to the ratio of reflected $p_r$ to incident $p_i$ acoustic pressure as follows:

$$R = \frac{p_I}{p_i} = \frac{Z_1 - Z_0}{Z_1 + Z_0} \tag{2}$$

In the case of propagation within a rigid tube of changing cross-sectional area A that is entirely filled with air, this relationship for R can be rewritten in terms of only areas via substitution of equation (1):

$$R = \frac{A_0 - A_1}{A_0 + A_1} \qquad (3)$$

Noting that for the case of a large increase in area at the boundary ($A_1 >> A_0$), R approaches $-1$ indicating a reflection that approaches the absolute amplitude of the incident pulse but is inverted. Conversely, for the case of a large decrease in area at the boundary ($A_1 << A_0$), R approaches $+1$ and thus the reflection would be expected to approach the amplitude of the incident pulse but not be inverted. If the pressure amplitude of a reflection from a boundary is measured and compared to the incident pressure amplitude, knowledge of the initial area $A_0$ can be used to estimate the area $A_1$ after the boundary, as can be seen by rearranging equation (3):

$$A_1 = \left[\frac{1-R}{1+R}\right] A_0 \text{ cm}^2 \qquad (4)$$

Figure 6:
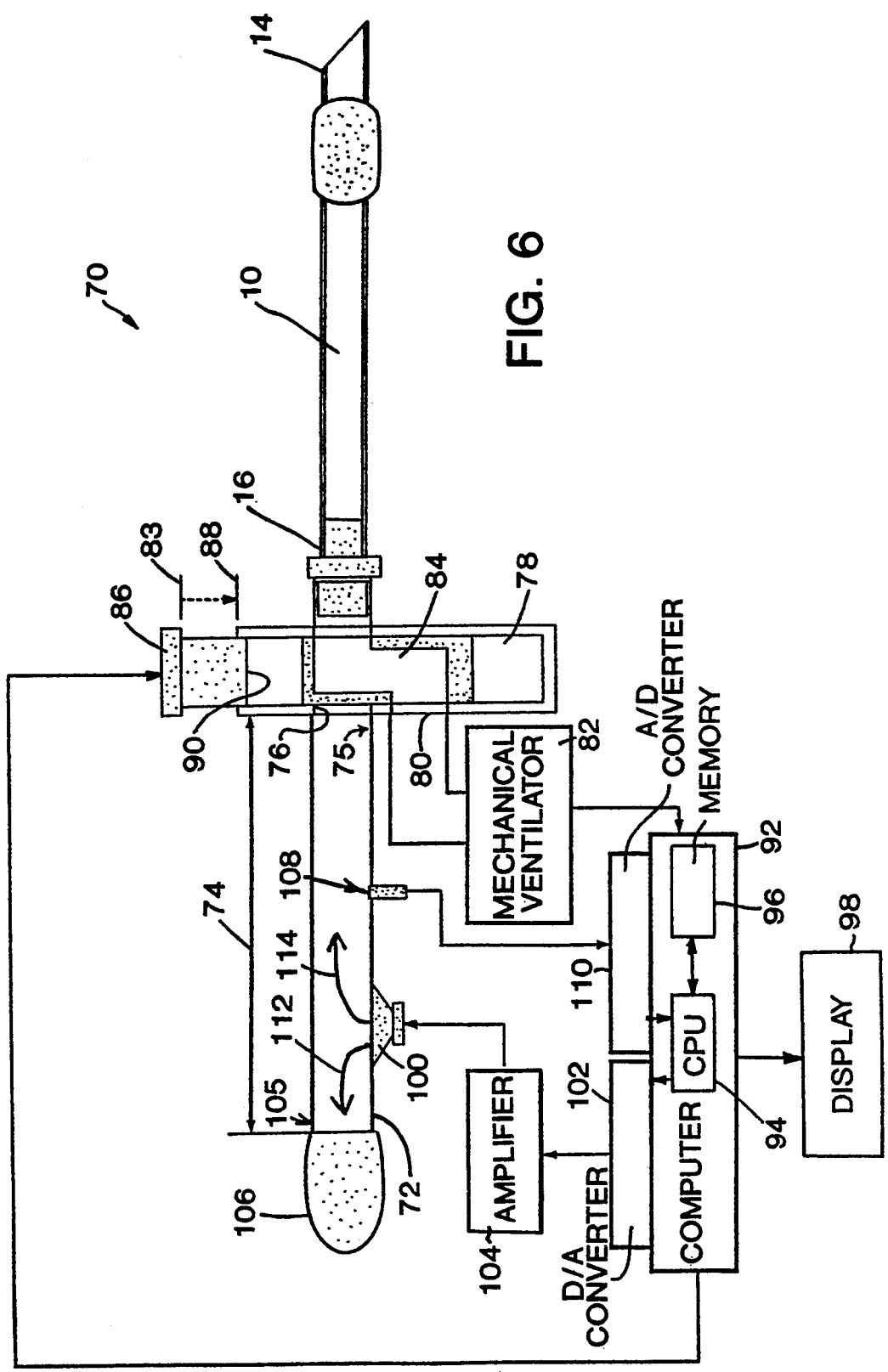
FIG. 6 is a diagrammatical view of the apparatus of the present invention for guiding a distal end of the ETT within a body.

FIG. 6 illustrates the apparatus 70 for acoustically guiding and monitoring the position of ETT 10 within a body. Apparatus 70 includes a wave guide 72 having a predetermined length 74. Illustratively, length 74 is 20 cm. A first end 75 of wave guide 72 is coupled to one input 76 of a valve 78. A second input 80 of valve 78 is coupled to a mechanical ventilator 82. Valve 78 is movable from a normal ventilating position 83 as illustrated in FIG. 6 so that passageway 84 of valve 78 provides communication between mechanical ventilator 82 and ETT 10. Valve 78 is also movable to an acoustical measurement position 88 by moving plunger 86 downwardly from its normal position 83. In the acoustical measurement position 88, passageway 90 of valve 78 provides communication between wave guide 72 and ETT 10. The approximate time in acoustical measurement (down) position 88 is 0.2 s, and then valve 78 is returned to the normal (up) position to provide a pathway between ETT 10 and mechanical ventilator 82. Mechanical ventilator 82 is coupled to a computer 92 which senses apneic periods to control movement of valve 78.

Computer 92 includes a central processing unit (CPU) 94 and an internal memory 96. Illustratively, computer 92 is a PC based computer including a 486 microprocessor (33 MHz) and display 98. Illustratively, computer 92 runs a customized, menu-driven program under a Windows format. It is understood, however, that computer 92 may be any microcontroller or microprocessor. In addition, although the illustrated embodiment is PC based, a hand-held unit containing a microprocessor or microcontroller along with an LCD display 98 may be used in accordance with the present invention. A speaker 100 is coupled to wave guide 72. Illustratively, speaker 100 is a driver model 150-50-8911 available from Sony. Speaker 100 is located in an outer wall of PVC wave guide 72. Computer 92 is coupled to an input of a digital-to-analog (D/A) converter 102. Illustratively, converter 102 is a WSB-100 and WSB-A12 module available from QuaTech. Converter 102 is an output coupled to an input of amplifier 104. An output of amplifier 104 is coupled to speaker 100. Illustratively, amplifier 104 is a model DRA345R available from Denon. Computer 92 therefore controls speaker 100 to generate incident pulses in wave guide 72. Incident pulses are short duration sonic pulses less than 120 dB SPL re 0.0002 μbar as measured in wave guide 72. Incident pulses have a duration of about 0.35 ms, and have a majority of spectral energy in a bandwidth between 500 and 1,500 Hz.

An acoustically absorptive material 106 is coupled to a second end 15 of wave guide 72. Illustratively, absorptive material 106 is made from a foam rubber material having a characteristic impedance closely matched to wave guide 72. A microphone 108 is coupled to wave guide 72 at a location between speaker 100 and first end 75 of wave guide 72. Illustratively, microphone 8 is a model EMC-155 available from Sony. Microphone 108 is coupled to an analog-to-digital (A/D) converter 110. An output of converter 110 is coupled to computer 92. Illustratively, converter 110 is a model DAS16 convertor available from Metrabyte.

Two pulses propagating in opposite directions emanate from speaker 100. A majority of the left-traveling sonic pulse in the direction of arrow 112 is absorbed by foam rubber material 106. The right-traveling incident pulse propagates down wave guide 72 in the direction of arrow 114. The incident pulse is recorded as it passes over microphone 108, and continues to propagate down and out of distal end 14 of ETT 10. Reflections of this incident pulse occur from within the airways and are recorded by microphone 108 as they propagate back up wave guide 72 and are finally absorbed by foam rubber material 106. If absorptive material 106 were not utilized, a portion of the incident sound energy would reflect back towards microphone 108 and temporally interfere with the recording of the desired airway reflections. The response of microphone 108 is flat to ±3 dB over the 50 Hz to 15 KHz frequency range. The analog output of microphone 108 is digitized by A/D converter 110 at a sampling rate of 100,000 samples/sec and is stored for analysis in memory 96 of computer 92.

The presence of a large inverted reflection from the acoustical end of the airways is used to assess that the ETT tip is in the trachea below the vocal folds and not in the posterior pharynx or esophagus. The time delay between detection of the incident and reflected pulses $t_d$ in ms is used to determine the distance between microphone 108 and the acoustical end of the airways d in cm assuming that the sound speed c is equal to that in a free field of air at body temperature, 35,000 cm/s=35.4 cm/ms:

$$d = \frac{ct_d}{2} \text{ cm} \qquad (5)$$

where the factor of two in the denominator is necessary to account for the sound pulse traveling both to and from the reflected boundary, a total distance of 2d.

The change in cross-sectional area arising between the ETT, $A_{ETT}$, and the airway or tube in which it is placed, $A_{Tube}$, is predicted to give rise to an additional reflection. The acoustic pressure amplitude of this tube tip reflection relative to that of the incident pulse is used to estimate the reflection coefficient, $R_{tip}$. The effective cross-sectional area of the airway or tube in which the ETT is placed is then indirectly estimated via equation (4)

$$A_{tube} = \left[\frac{1 - \alpha R_{tip}}{1 + \alpha R_{tip}}\right] A_{ETT} \text{ cm}^2 \qquad (6)$$

where the calibration coefficient $\alpha$ is found before intubation by inserting the ETT into a tube with known cross-sectional area $A_{known}$, estimating the reflection coefficient $R_{tip}$ by taking an acoustical measurement, and then calculating:

$$\alpha = \left[ \frac{1 - \frac{A_{known}}{A_{ETT}}}{1 + \frac{A_{known}}{A_{ETT}}} \right] \frac{1}{R_{tip}} \quad (7)$$

Of course, if one desires an estimated diameter, it is easily calculated by using the formula relating the diameter of a circle to the area, $A = \pi(\text{diameter}/2)^2$.

An additional capability of detecting the buildup of airway fluids inside the ETT can indicate when an ETT requires suctioning. Any significant mucous buildup along the inner walls of the ETT would alter the constant ETT cross-sectional area and is detected by examining the reflections, if any, that precede in time the tube tip reflection. Using these reflections, the locations and amounts of excess mucous along the inner ETT walls are then estimated using equations (5) and (6).

Figure 19:
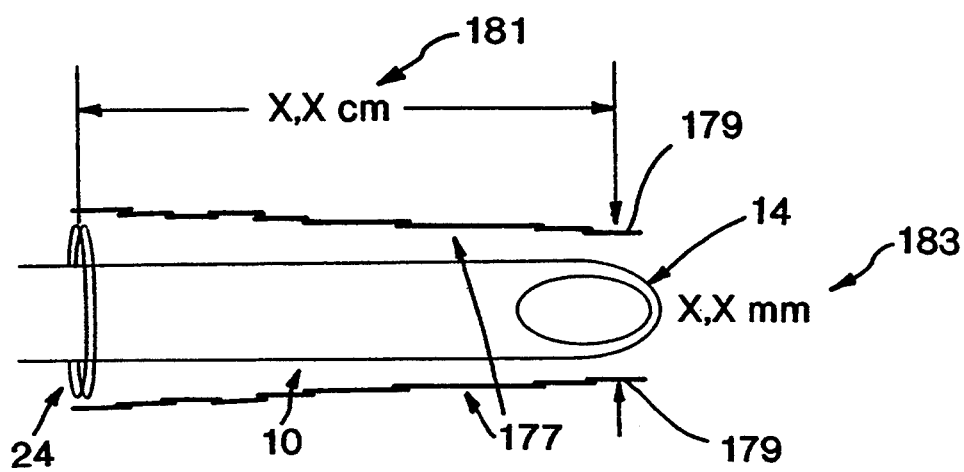
FIG. 19 is a diagrammatical view illustrating a visual display of the apparatus to provide visual indication to the user of the distance of insertion and of the estimated diameter of a body conduit into which the ETT is inserted.

After the estimated insertion distance and estimated airway diameter have been calculated by the system, they are presented to the user in the convenient graphical format depicted in FIG. 19. This display consists of pictorial representation of ETT 10, a marker of the estimated position of vocal folds 24 in relation to the ETT tip, and boundary markers on either side of the ETT tip representing the estimated diameter of the airway at the tube tip. All movements of ETT 10 within the airway are reflected on the system display. Also, all previously estimated airway diameter markers 177 remain displayed at their corresponding position along ETT 10 which provides the user with a rough outline of the airway dimensions between the vocal folds 24 and the tube tip.

Figure 7:
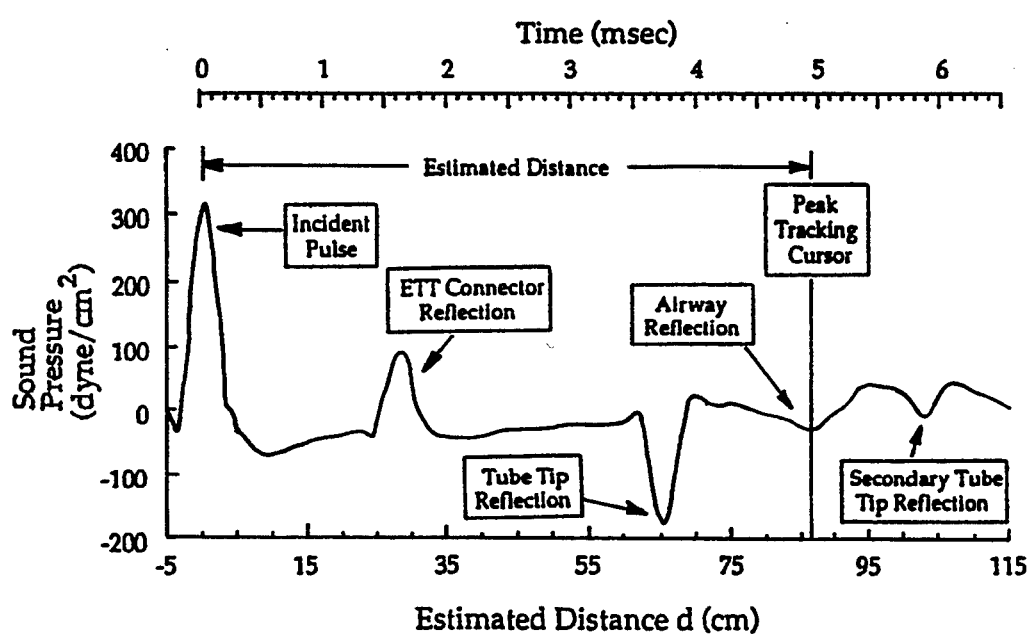
FIG. 7 is a graphical representative acoustical measurement for endotracheal intubation of the incident pulse and of reflected pulses from the airways recorded by a microphone.

The apparatus 70 was evaluated through multiple intubation procedures on six anaesthetized canines who were undergoing surgery. The experimental protocol was as follows. The guidance system was engaged in a free-running mode prior to intubation with a repetition rate of 5 pulse/s. The intubation procedure was then initiated and an ETT of 1 cm inner diameter was advanced slowly into the vocal tract toward the vocal folds. When the ETT tip passed through the vocal folds, the inverted reflection from the acoustical end of the airways was detected via an algorithm that searched for the temporal location of the inverted reflection (minima) with absolute amplitude greater than 20% of the incident pulse in a window between 0.25 and 2 ms after the tube tip reflection. A representative measurement by microphone 108 of an incident pulse and reflected pulses is illustrated in FIG. 7. FIG. 7 illustrates a positive ETT connector reflection pulse and a sizable, inverted reflection resulting from the acoustical boundary as predicted by the "horn" model of the airways. Also, there is an inverted reflection due to the change in A between the distal tip 14 of ETT 10 and the airway, as is expected from the acoustical impedance considerations.

Figure 8:
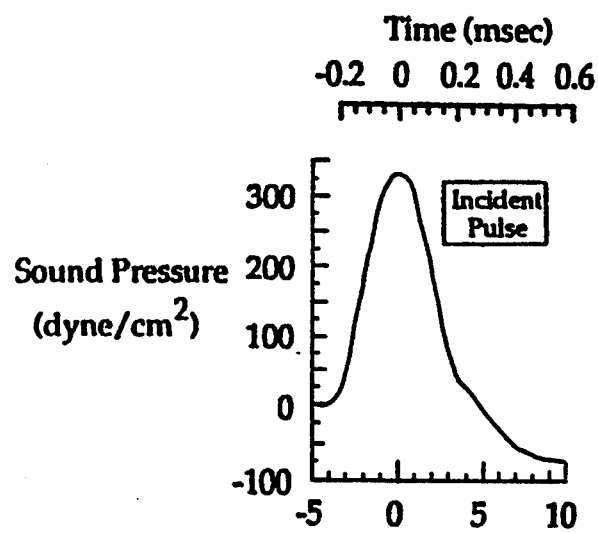
FIG. 8 is a graphical illustration of an acoustical measurement of an incident pulse transmitted by a speaker through a wave guide, through the ETT, and into the airways of respiratory system.
Figure 9A:
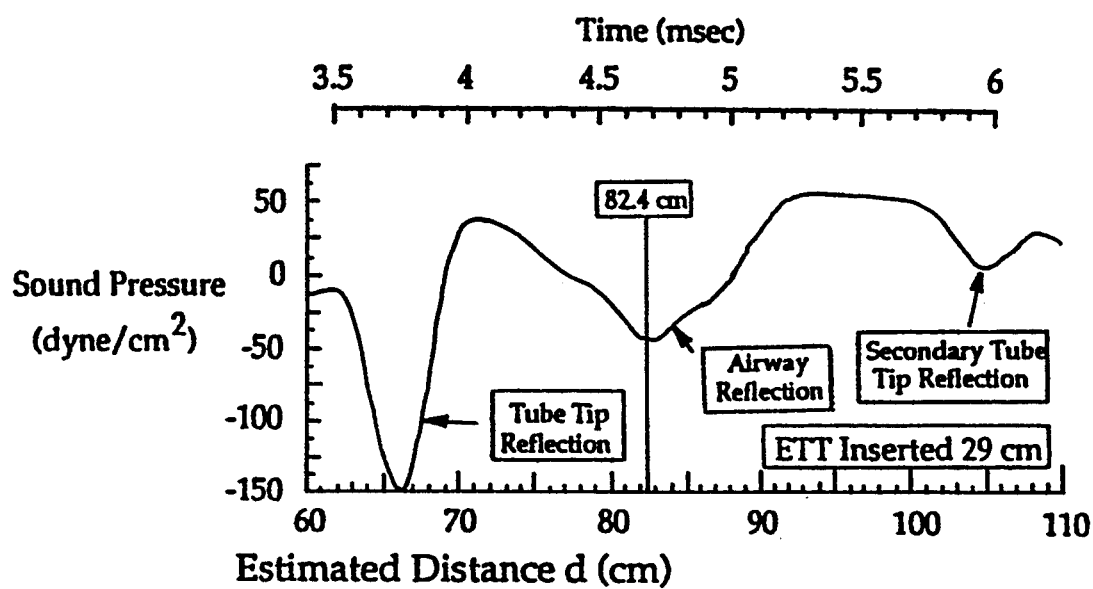
FIG. 9a–9c are graphical illustrations of acoustical measurements of reflected sound pulses taken at three different ETT insertion distances in a trachea.
Figure 9B:
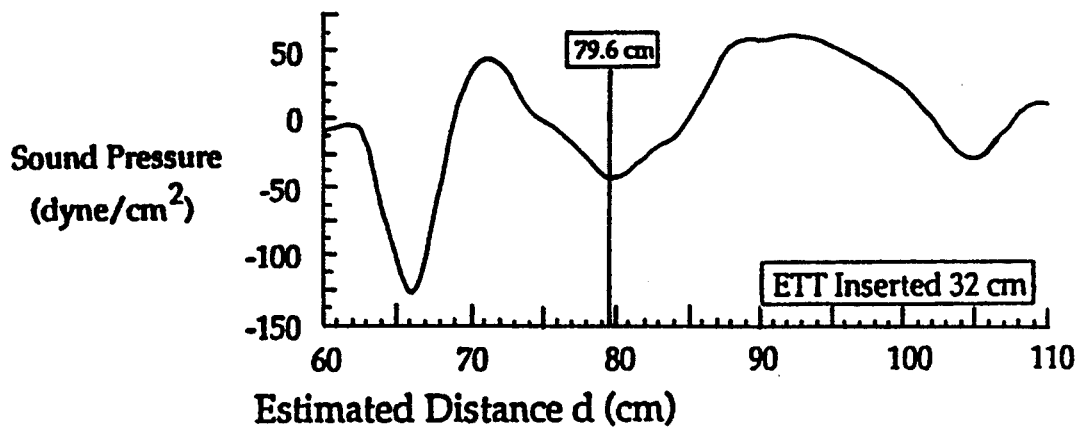
Figure 9C:
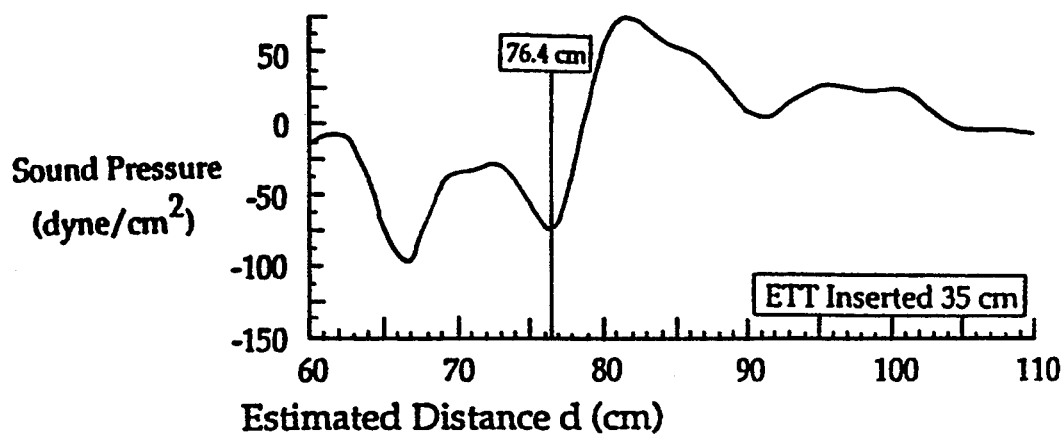

Once the airway reflection was detected, ETT 10 was advanced at 1 cm increments further into the airways and the system estimated the distance d from the acoustical signal using equation (5) at each increment. FIG. 8 illustrates a incident pulse generated by speaker 108. FIGS. 9a–9c illustrate the measured acoustical signals as a function of the estimated distance from microphone 108 to the boundary that caused the reflection at three different insertion distance 3 cm apart. Note as ETT 10 moves further into the airways, the reflected pulse from the airway moves a corresponding estimated distance closer to the incident pulse, while the reflection from the ETT tip/airway boundary does not change its relative location of roughly 66 cm from microphone 108. Also note that the amplitude of the ETT tip reflection decreases with insertion distance due to the decreasing tracheal A immediately following the tip.

Figure 10:
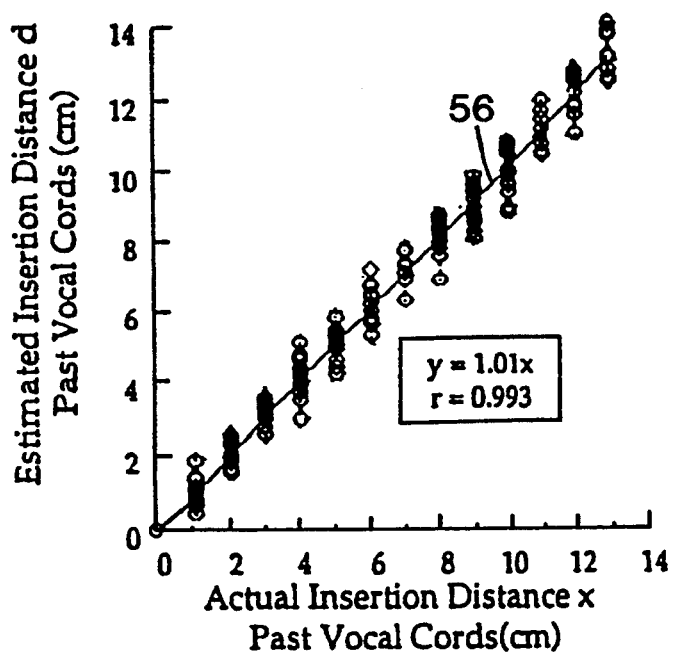
FIG. 10 is a graph illustrating estimated insertion distances calculated by the apparatus of the present invention compared with actual insertion distances illustrating the accuracy of the present invention.

The distal end 14 of ETT 10 was advanced as far below the vocal folds as possible, roughly 15–20 cm, and then removed also at 1 cm increments with estimates of d performed at each step. FIG. 10 illustrates the relationships between the actual ETT movement distances past the vocal folds and the acoustically estimated d over multiple procedures in six canines. To form FIG. 10, when a lock was achieved just past the vocal folds, the estimated value of d and the actual insertion distance x were set equal to 0, so that d vs. x could be plotted over the subsequent incremental measurements. Line 56 in FIG. 10 is a plot of the best fit line through the data points. Line 56 has a slope of 1.01. A totally accurate tracking would have a slope of 1.00.

Figure 11:
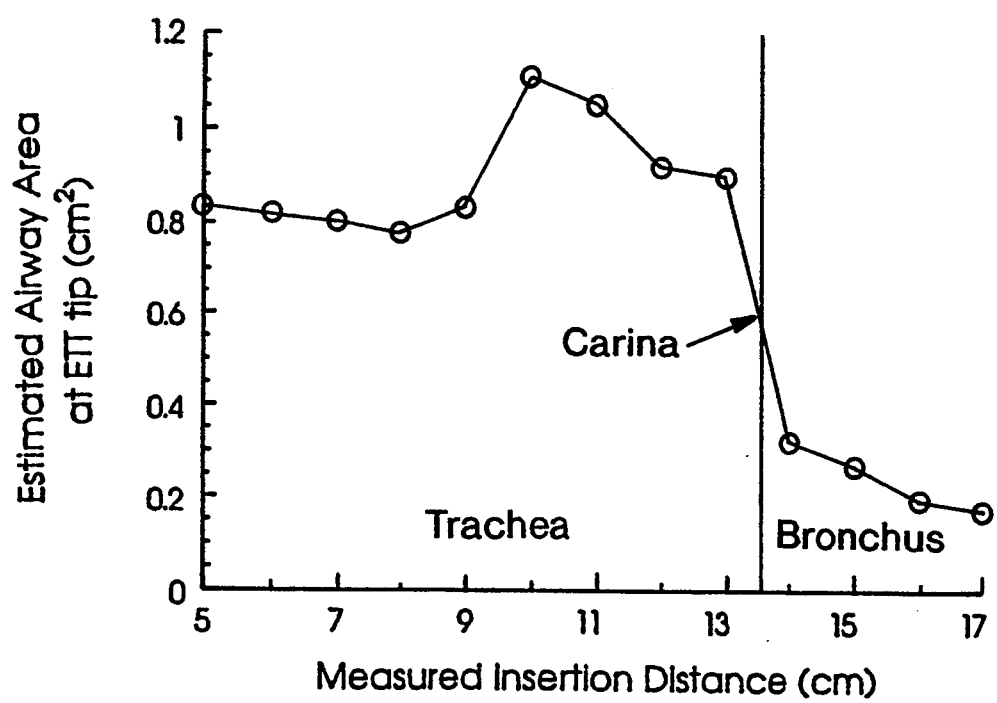
FIG. 11 is a graphical illustration of an estimated airway area calculated by the apparatus of the present invention during insertion of the ETT into the trachea, and past the carina into a main bronchus.

To determine if the acoustical system could discriminate between tracheal and bronchial intubations, the evaluation procedure was performed on two canines using an elongated ETT 10 under fluoroscopic guidance. In each case, the location of the carina was estimated by advancing the ETT tip into both the right and left bronchi and noting the point when lateral movement of the tip was observed. This anatomic landmark was then referenced via the 1 cm markings on the ETT to the canine's eye tooth, and the complete intubation procedure was performed at 1 cm increments as previously described. At each increment, an estimate of the cross-sectional area of the airway, $A_{tube}$, was made from the amplitude of the tube tip reflection via equation (6). FIG. 11 illustrates the estimated $A_{tube}$ as a function of insertion distance past the vocal folds (X - X₀) for a case where the carina was estimated to be at an insertion distance of roughly 13.5 cm. At that point, $A_{tube}$ changes from the tracheal cross-sectional area of approximately 0.9 cm² to the smaller bronchial area of about 90.3 cm², over an insertion distance 2 cm. This large change in acoustically estimated area allows the detection of ETT tip movement past the carina.

Figure 12A:
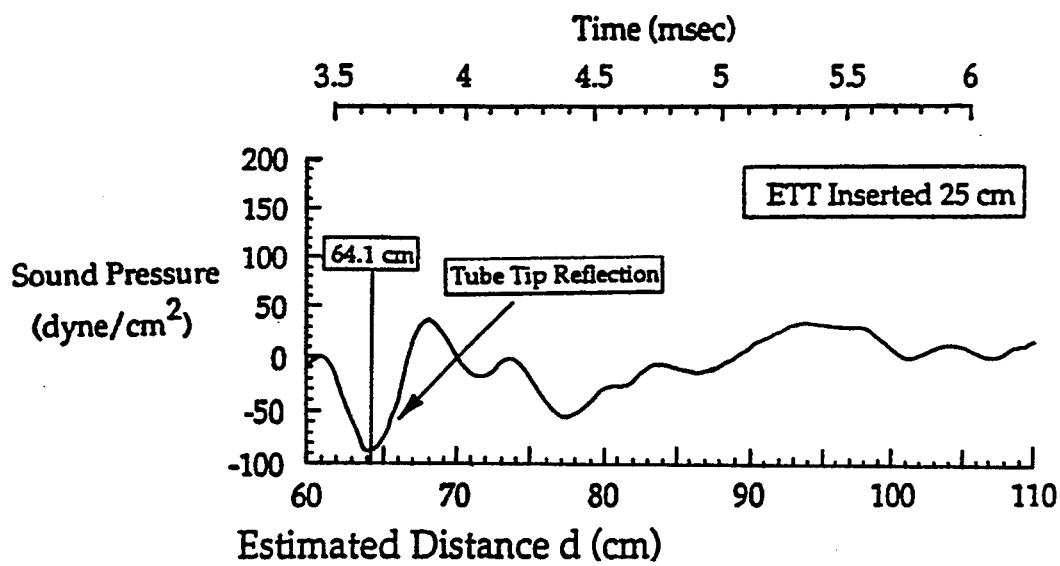
FIGS. 12a–12c are graphical illustrations of acoustical measurements of reflected sound pulses taken at three different ETT insertion distances when the ETT was inserted into an esophagus.
Figure 12B:
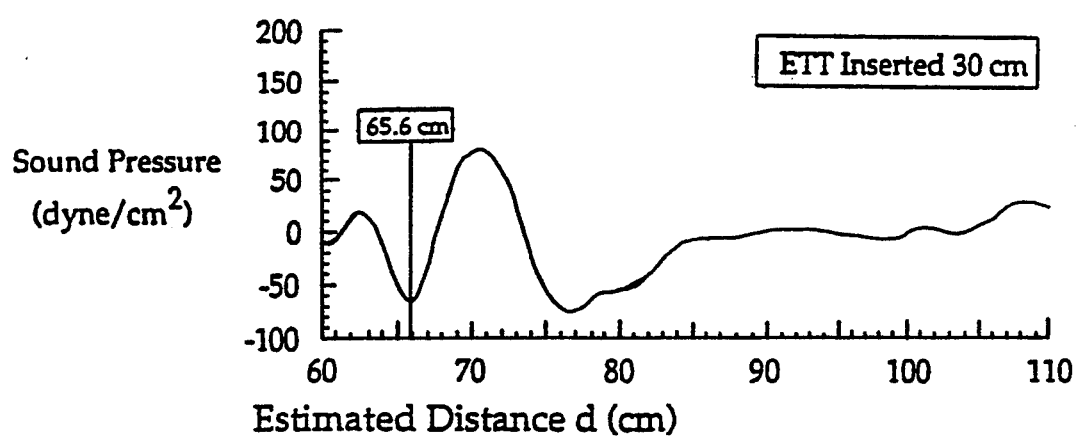
Figure 12C:
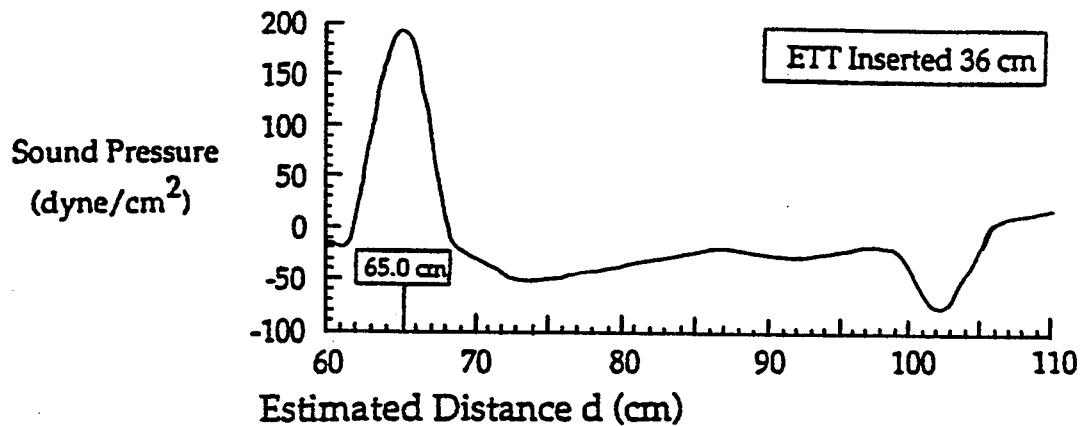

If the ETT was advanced into the esophagus, the acoustical reflections that were observed were different in character than those previously described for tracheal intubation. FIGS. 12a–12c illustrate acoustical waveforms recorded at three different insertion distances during esophageal intubation. As compared to the more rigid trachea, the esophagus is a collapsible tube. Thus, from an acoustical perspective, the reflections took on two distinctly different characteristics when compared to the airway reflections: 1) the reflection from the tube tip was typically erratic in amplitude and often times it was not inverted (see FIG. 12c). The erratic amplitude of the tube tip reflection could be explained by the ever-changing cross-sectional A formed by the compliant esophageal walls around the advancing ETT tip. The non-inverted reflection indicated that the $A_{ETT}$ was essentially equal to or greater than the effective cross-sectional area of the esophagus, a relationship that is not observed for intubations into a larger and more rigid trachea. 2) Multiple small amplitude reflections were occasionally observed immediately following the ETT tip reflection that remained over a broader time period as compared to the distinct inverted airway reflection (see FIG. 12a). These multiple reflections are indicative of the collapsed nature of the esophagus immediately in front of the ETT tip giving rise to successive reflections of the pulse at the point of collapse and the boundary between the ETT and the esophagus. In all of the esophageal intubations that were performed, these two major differences in the nature of the acoustic reflections allowed discrimination between these and a successful tracheal intubation.

Figure 13:
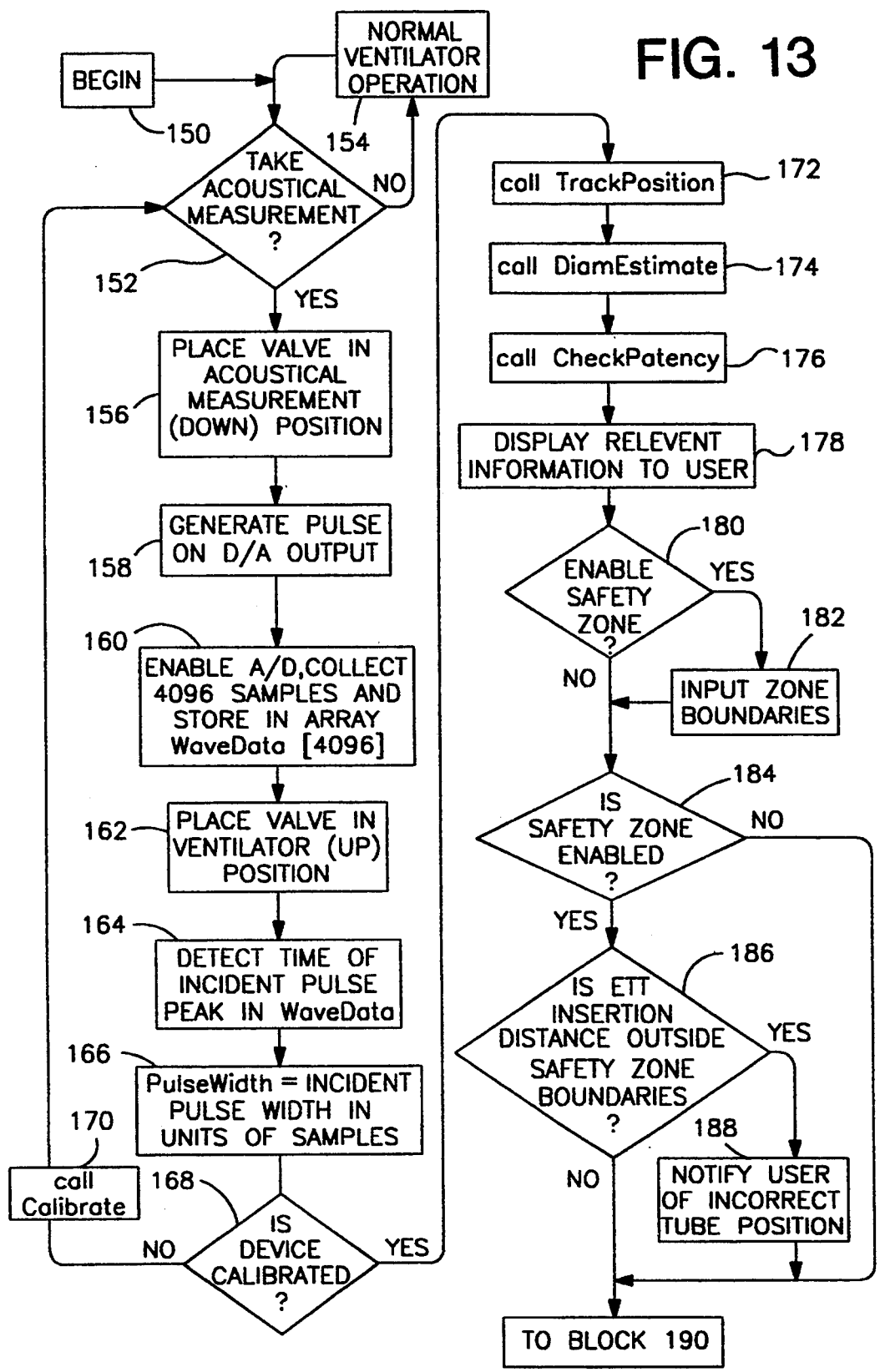
FIG. 13 is a flow chart illustrating the steps performed by the apparatus of the present invention for guiding and monitoring the position of the ETT within the body.

FIGS. 13–18 illustrate operation of the apparatus and method of the present invention for guiding and monitoring tube such as ETT 10 within a body. As illustrated in FIG. 13, operation begins at block 150. Computer 92 determines whether or not to take an acoustical measurement at block 152. Computer 92 can be programmed to take acoustical measurements at preset time intervals ranging up to about ten times per second. Alternatively, a manual switch may be provided to activate the acoustical measurement system. In the manual setting, mechanical ventilator 82 provides normal ventilation to ETT 10 until the manual key is entered. If an acoustical measurement is not to be taken at block 152, mechanical ventilator 82 continues normal ventilation as illustrated at block 154.

If computer 92 indicates that an acoustical measurement is to be made at block 152, computer 92 controls movement of valve 78 so that second passageway 90 of valve 78 provides communication between wave guide 72 and ETT 10 as illustrated at block 156. Computer 92 then supplies a pulse to D/A converter 102 as illustrated at block 158. The analog pulse output from converter 102 passes through amplifier 104 to speaker 100. A portion of the pulse propagating in direction of arrow 112 in wave guide 72 is substantially absorbed by absorptive material 106. An incident pulse travelling in the direction of arrow 114 in FIG. 6 propagates through wave guide 72, through passageway 90 of valve 78, through ETT 10, and into the body. An illustrative incident pulse is illustrated in FIG. 8. Microphone 108 records the incident pulse as it moves past microphone 108 and also records reflected pulses as discussed above in detail. Computer 92 then enables A/D converter 110, collects 4,096 data samples detected by microphone 108, and stores the data in an array of computer memory 96 as illustrated at block 160. Computer 92 then controls movement of valve 78 back to its normal ventilator position 83 as illustrated at block 162. Computer 92 detects the time of an incident pulse peak from the stored array in computer memory 96 as illustrated at block 164. Computer 92 uses a peak detector to determine the maximum value of the incident pulse peak and sets the time of the pulse peak as t0. Computer 92 then determines the pulse width of the incident pulse as illustrated at block 166. Computer 92 detects the number of samples occurring between zero voltage crossing locations on opposite sides of the incident pulse peak and sets this number equal to the pulse width. The pulse width is stored in memory 96 of computer 92.

Computer 92 then determines whether the device is calibrated at block 168. If the device is not calibrated, computer 92 calls a calibration subroutine 17 at block 170. Calibration of the device will be discussed in detail below with reference to FIG. 15. If the device is calibrated at block 168, computer 92 calls a TrackPosition subroutine at block 172 to detect the position (insertion distance) of distal end 14 of ETT 10 within the body. Computer 172 then calls subroutine DiamEstimate as illustrated at block 174. This subroutine estimates a diameter of the larger body conduit or cavity into which ETT 10 is inserted. Computer 92 then checks the patency of ETT 10 by calling subroutine CheckPatency at block 176. During this subroutine, computer 92 determines whether or not ETT 10 is obstructed. Computer 92 then displays relevant information to the device user as illustrated at block 178. As illustrated in FIG. 19, the display screen 98 provides an image representing ETT 10 and distal end 14. Display 98 also indicates the location of vocal folds 24. Lines 177 on opposite sides of ETT 110 indicate previously measured airway diameters relative to ETT 10. Current measured airway diameters are located adjacent tip 14 as indicated at locations 179. Display 98 also provides a numerical insertion distance for distal end 14 of ETT 10 as illustrated at location 181. Finally, display 98 provides a numerical estimated diameter of the body conduit or cavity in which ETT 10 is inserted as illustrated at location 183.

After relevant information is displayed at block 178, computer determines whether a safety zone has been enabled at block 180 of FIG. 13. If the safety zone is enabled, safety zone boundaries are input at block 182. The boundaries can be manually inserted by a user or can be preprogrammed into the device. The safety zone is designed to alert a user if distal end 14 of ETT 10 moves beyond an initial position by a preset amount defined by the safety zone limits. If an operator does not want to enable the safety zone, computer 92 moves directly to block 184 without setting zone boundaries. Computer 92 determines whether the safety zone is enabled at block 184. If the safety zone is enabled, computer 92 determines whether the ETT insertion distance is outside the safety zone boundaries at block 186. The insertion distance used at block 186 was calculated previously at block 172. If the ETT insertion distance is outside the safety zone boundaries, computer 92 sounds an alarm to alert the user of an incorrect tube position as illustrated at block 188. If the ETT insertion distance is within the safety zone boundaries, computer 92 advances to block 190 of FIG. 14. If the safety zone is not enabled at block 184, computer 92 advances directly to block 190 in FIG. 14.

Figure 14:
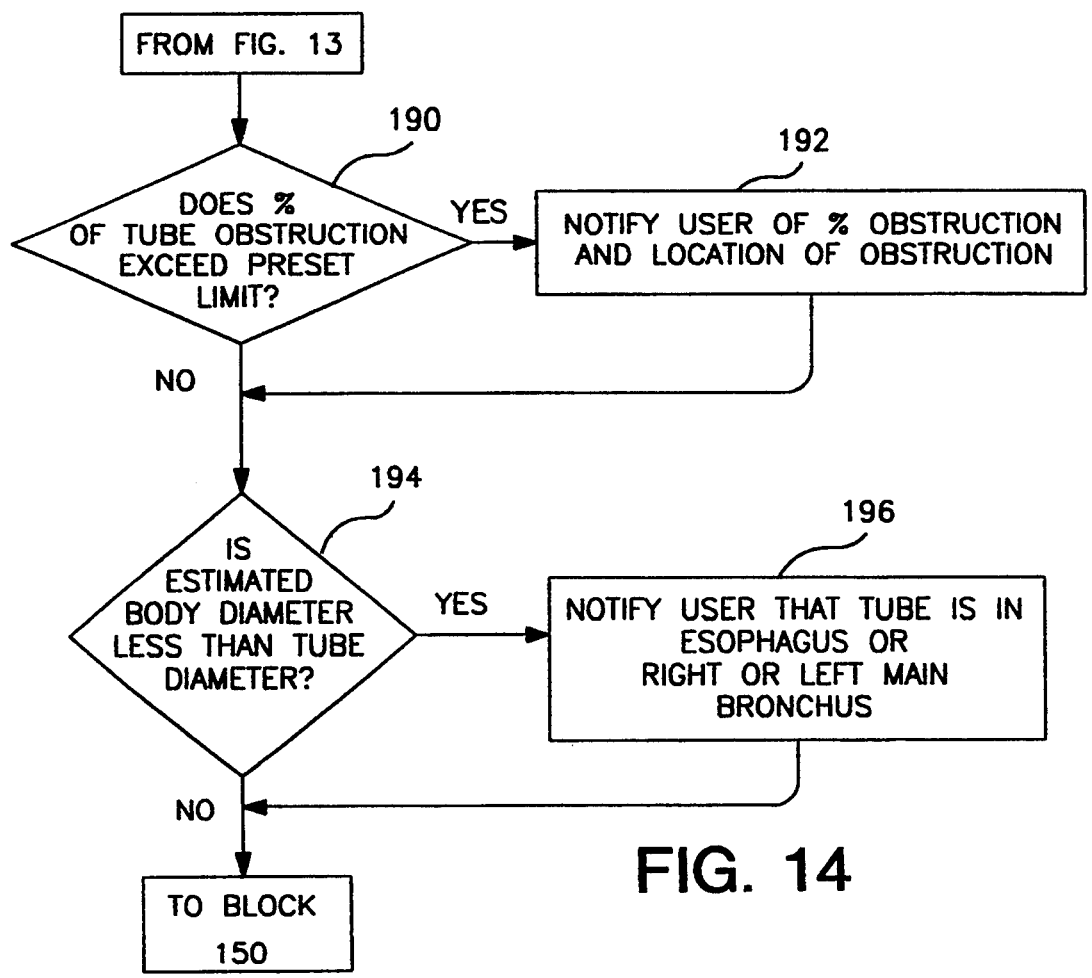
FIG. 14 is a flow chart illustrating additional steps performed by the apparatus.

As illustrated in FIG. 14, computer 92 determines whether the percentage of tube obstruction calculated at block 176 exceeds a preset limit. Again, the preset limit can be preprogrammed into computer 92 or set manually by an operator. If the percentage of tube obstruction exceeds the preset limit at block 190, computer 92 notifies the user of the amount of obstruction and the location of the obstruction at block 192. An alarm is also sounded to alert the user. If the percentage of tube obstruction does not exceed the preset limit at block 190, computer 92 determines whether the estimated diameter of the body calculated at block 174 is less than a diameter of ETT 10 at block 194. If the estimated body diameter is less than ETT 10 diameter, computer 92 notifies the user that the ETT 10 is located in the esophagus, the right main bronchus, or the left main bronchus as illustrated at block 196. An alarm also sounds to alert the user of the improper location of ETT 10. If the estimated body diameter is not less than ETT 10 diameter, computer 92 advances back to block 150 of FIG. 13 to proceed through the operation loop again.

Figure 15:
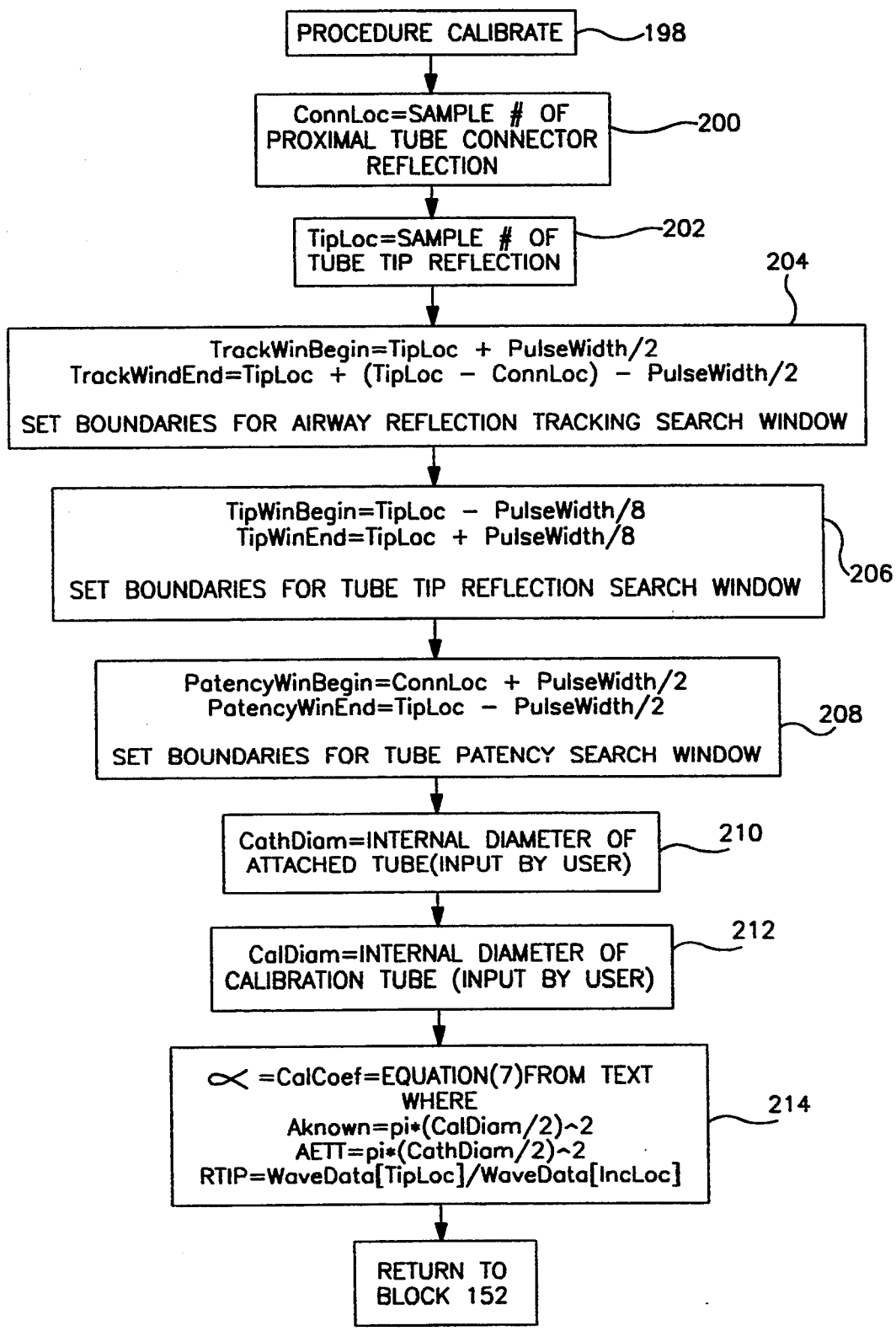
FIG. 15 is a flow chart illustrating the steps performed by the apparatus during a calibration procedure.

The calibration subroutine called at block 170 of FIG. 13 is illustrated in FIG. 15. The calibration procedure begins at block 198. During the calibration procedure, ETT 10 is inserted into a calibration tube having a known internal diameter. Computer 92 first detects the location of the proximal end of ETT 10 by detecting the peak location of a positive reflection pulse illustrated in FIG. 7. The variable "ConnLoc" is set to the time of the detected peak of ETT connector reflection at block 200. Computer 92 then detects the location of the tip of distal end 14 of ETT 10 by determining the location of the peak of tube tip reflection in FIG. 7. The variable "TipLoc" is set to the time of the tube tip reflection peak at block 202. The time between the incident pulse peak, the ETT connector reflection, and the tube tip reflection remains constant throughout the procedure. This is because the distance between microphone 108 and distal end of ETT 10 is fixed.

Computer 92 then sets the boundaries for an airway reflection tracking search window at block 204. The starting time for the airway tracking window is set as TrackWinBegin=TipLoc+PulseWidth/2. The ending time for the airway reflection tracking search window is set as TrackWinEnd=TipLoc+(TipLoc−ConnLoc)−PulseWidth/2 as illustrated in block 204.

Computer 92 then sets the boundaries for a tube tip reflection search window at block 206. The starting time for the tip reflection search window is set as TipWinBegin=TipLoc−PulseWidth/8. The ending time for the tip reflection search window is set as TipWinEnd=TipLoc+PulseWidth/8 as illustrated in block 206.

Next, computer 92 sets the boundaries for a tube patency search window at block 208. The starting time for the patency search window is set as PatencyWinBegin=ConnLoc+PulseWidth/2. The ending time for the patency search window is set as PatencyWinEnd=TipLoc−PulseWidth/2 as illustrated in block 208.

Computer 92 then sets a variable "CathDiam" equal to the internal diameter of ETT 10 "CathDiam" at block 210. Illustratively, this internal diameter of ETT 10 may be input by a user or preprogrammed into computer 92 for use with a particular size ETT 10. Computer 92 then sets variable "CalDiam" equal to the internal diameter of the calibration tube at block 212. Again, the internal diameter of calibration tube can be manually set by a user or preset for use with a specific size calibration tube. As illustrated at block 214, computer 92 then calculates a calibration coefficient from equation (7) discussed above and then returns to block 152 of FIG. 13.

Figure 16:
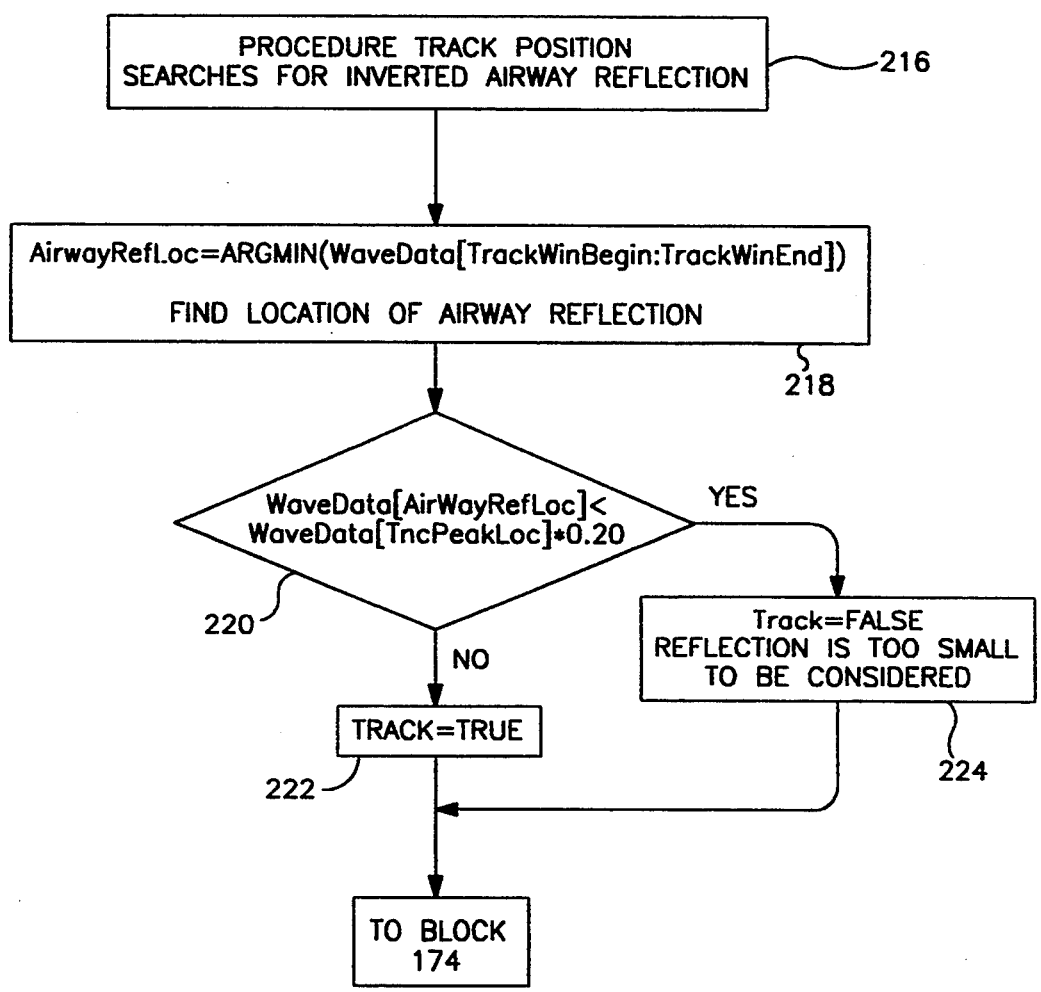
FIG. 16 is a flow chart illustrating the steps performed by the apparatus to detect a position of a distal end of the ETT within the body.

The subroutine for monitoring the position of distal end 14 of ETT 10 is illustrated in FIG. 16. Subroutine TrackPosition begins at block 216 to search for an inverted airway deflection illustrated in FIG. 7. Computer 92 first finds the location of the airway reflection by determining the sample data point within the airway reflection tracking search window set at block 04 during the calibration stage from the stored data in memory 96 of computer 92. This step is illustrated at block 218. Computer 92 then determines at block 220 whether the minimum value detected at block 218 is less than 20 percent of the peak value of the incident pulse. If the detected minimum value of the airway reflection is not less than 20 percent of the maximum value of the incident pulse, computer 92 indicates at block 222 that the detected airway reflection minimum value is valid. Computer 92 then advances to block 174 of FIG. 13. If computer 92 determines that the detected minimum airway reflection value is less than 20 percent of the maximum incident pulse value at block 220, computer 92 determines that the detected airway reflection is too small to be considered a valid reflection. This step is illustrated at block 224. Computer 92 then advances to block 174 of FIG. 13.

Figure 17:
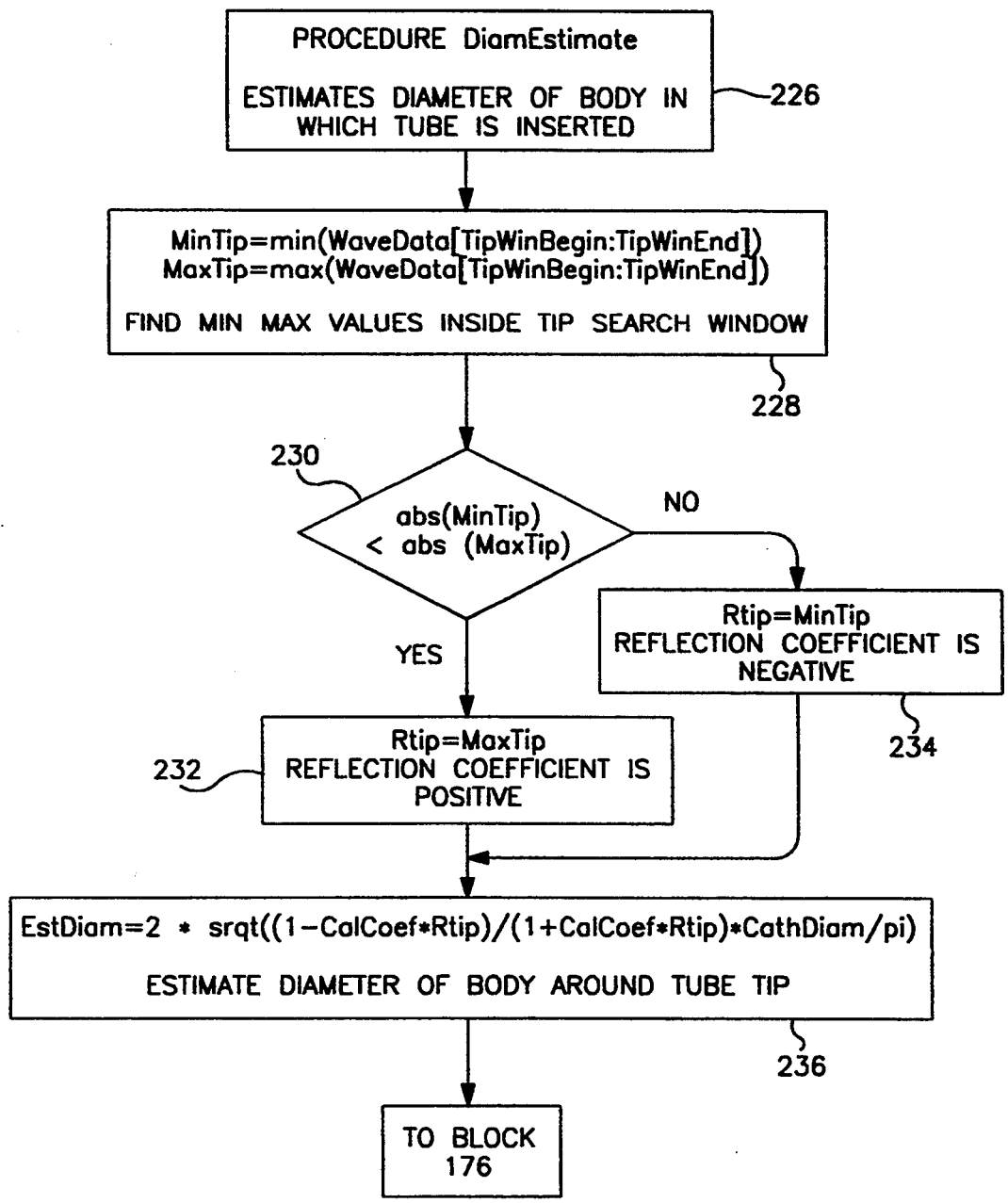
FIG. 17 is a flow chart illustrating the steps performed by the apparatus for calculating an estimated diameter of the body in which the ETT is inserted.

The procedure for estimating a diameter of the body in which ETT 10 is inserted is illustrated in FIG. 17. Procedure DiamEstimate begins at block 226 of FIG. 17. Computer 92 first determines the minimum and maximum values within the tube tip reflection search window established at block 206 of the calibration procedure. The variable "MinTip" is set equal to the minimum value of the data stored in computer memory 96 over the preset tube tip reflection search window range. The variable "MaxTip" is set to the maximum stored value within the tube tip reflection search window range. This step is illustrated at block 228. Computer 92 then determines whether the absolute value of the minimum value (MinTip) is less than the absolute value of the maximum value (MaxTip) at block 230. If the absolute value of the detected minimum is less than the absolute of the detected maximum, the reflection coefficient Rtip is set equal to Max Tip as illustrated at block 232. This indicates that the reflection coefficient Rtip is positive. A positive reflection coefficient indicates that the diameter of the body surrounding ETT is less than the diameter of ETT. In other words, distal end 14 of ETT 10 has been inserted into either in the esophagus, the right primary bronchus, or the left primary bronchus. If the absolute value of the detected minimum is greater than the absolute value of the detected maximum at block 230, computer 92 sets the reflection coefficient Rtip equal to Mintip. Therefore, the reflection coefficient Rtip is a negative value. This step is illustrated at block 234. Computer 92 then estimates the diameter of the body surrounding distal end 14 of ETT 10 using the formula as illustrated at block 236. Computer 92 then returns to block 176 of FIG. 13.

Figure 18:
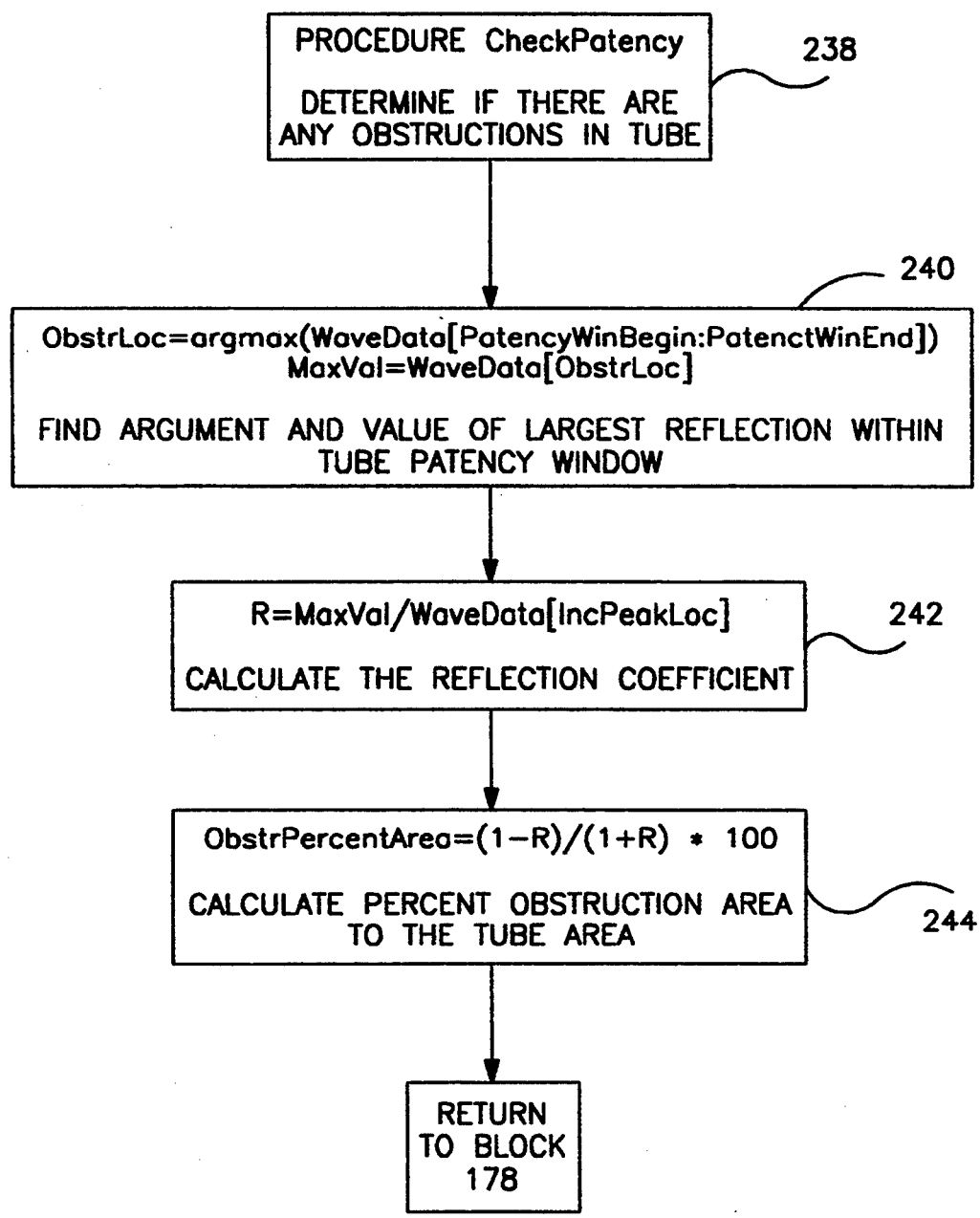
FIG. 18 is a flow chart illustrating the steps performed by the apparatus to determine if the inserted ETT is obstructed.

The procedure for checking the patency of distal end 14 of ETT 10 is illustrated in FIG. 18. In other words, computer 92 determines whether mucous builtup or other obstructions are partially blocking ETT 10. Procedure "CheckPatency" begins at block 238 of FIG. 18. Computer 92 first finds an argument and the value of the largest reflection within the tube patency window established at block 208 during a calibration procedure. This step is illustrated at block 240. Computer 92 first sets variable "ObstrLoc" equal to the time of the maximum value of the stored wave data in memory 96 of computer 92 over the range of values in the patency search window. Computer 92 then sets variable "MaxVal" equal to the value of the sampled data point at time="ObstrLoc". Computer 92 then calculates the reflection coefficient R at block 242. The reflection coefficient R is equal to the "MaxVal" value set at block 240 divided by the value of the stored data at the incident pulse peak time. Computer 92 then calculates the percentage obstruction area compared to the total ETT area at block 244. Computer 92 then returns to block 178 of FIG. 13.

Although the method and apparatus described is related to guiding and positioning an ETT 10 within a respiratory system of a body, it is understood that the apparatus and method of the present invention may be used to guide insertion of hollow tubes or catheters into other body cavities or in various mechanical operations. The acoustical guidance apparatus and method can be applied to a wide variety of clinical tubes or catheters where accurate placement and position monitoring is required. For example, the apparatus and method can be used to ensure proper feeding tube placement in the stomach and not in the esophagus or small intestine. The apparatus and method can be used to determine the location of a urinary catheter for diagnosis and relief of incontinence or for other reasons. The apparatus and method can also be used to position arterial and venous catheters to measure physiological parameters and deliver therapeutic pharmaceuticals. Also illustratively, the apparatus and method can be used to monitor the position of indwelling heart catheters used in hemodynamic clinical studies.

The general method required to employ acoustical guidance according to the apparatus and method of the present invention requires certain specific steps to be followed. First, the acoustical properties of the medium in which the sound pulses will be propagated must be analyzed and determined. For example, sound speed and acoustic losses in the medium such as blood, air, or urine must be determined. The next step of the method is to determine the acoustic wall properties of the body conduit in which the tube or catheter will reside. Properties such as compliance, mass, and resistance must be determined for the conduit or cavity into which the tube or catheter is inserted. Next, anatomical boundaries that give rise to specific identifiable reflections must be determined. For instance, a pulse may reflected off a valve between the bladder and urethra when inserting a tube or catheter into the bladder. Next, amplitude requirements for exogenous sound pulses to be delivered to ensure detectable reflections from the key boundaries must be determined. The operator must also determine pulse width and shape (and therefore frequency content) to optimize reflections from boundaries of interest to allow calculations of distances, dimensions, etc. to be made. Finally, particular sound generators such as speakers, detectors such as microphones, wave guides, absorptive material, connectors, and valves must be coupled together to propagate sound forces into a body, detect reflected pulses, and process the detected pulses.

Although the invention has been described in detail with reference to a certain preferred embodiment, variations and modifications exist within the scope and spirit of the invention as described and defined in the following claims.

What is claimed is:

1. An apparatus for acoustically guiding a distal end of a tube within a body, the apparatus comprising:
    a wave guide coupled to a proximal end of the tube;
    a mechanical ventilator;
    a valve movable from a first position to provide communication between the wave guide and the proximal end of the tube to a second position to provide communication between the mechanical ventilator and the proximal end of the tube;
    a speaker coupled to the wave guide for generating an incident sound pulse in the wave guide which propagates into the body;
    a microphone coupled to the wave guide between the speaker and the tube for detecting sound pulses moving past the microphone in the wave guide from the incident sound pulse and from reflected sound pulses from within the body; and
    means for processing the sound pulses detected by the microphone to guide insertion of the distal end of the tube within the body.

2. The apparatus of claim 1, wherein the processing means includes means for providing an indication of the position of the distal end of the tube within the body.

3. The apparatus of claim 2, further comprising means for monitoring the position of the distal end of the tube within the body, the monitoring means generating a warning signal if the distal end of the tube moves beyond a preset zone.

4. The apparatus of claim 1, wherein the processing means includes means for estimating dimensions of the body adjacent the distal end of the tube.

5. The apparatus of claim 4, further comprising means for generating a warning signal if the dimensions estimated by the estimating means are smaller than dimensions of the distal end of the tube.

6. The apparatus of claim 1, wherein the processing means includes means for determining if the tube is obstructed.

7. The apparatus of claim 6, further comprising means for generating a warning signal if the tube is obstructed by more than a predetermined percentage.

8. The apparatus of claim 1, further comprising an absorptive material coupled to an end of the wave guide for substantially absorbing sound pulses moving toward the end of the wave guide.

9. The apparatus of claim 1, further comprising means for displaying information generated by the processing means.

10. An apparatus for acoustically guiding a distal end of a tube within a body, the apparatus comprising:
    means coupled to a proximal end of the tube for generating an incident sound pulse in the tube which propagates into the body;
    a mechanical ventilator;
    a valve movable from a first position to provide communication between the generating means and the proximal end of the tube to a second position to provide communication between the mechanical ventilator and the proximal end of the tube;
    means for detecting sound pulses in the tube resulting from the incident sound pulse and from reflected sound pulses from within the body; and
    means for processing the detected sound pulses to guide insertion of the distal end of the tube within the body.

11. The apparatus of claim 10, wherein the processing means includes means for providing an indication of the position of the distal end of the tube within the body.

12. The apparatus of claim 11, further comprising means for monitoring the position of the distal end of the tube within the body, the monitoring means generating a warning signal if the distal end of the tube moves beyond a preset zone.

13. The apparatus of claim 10, wherein the processing means includes means for estimating dimensions of the body adjacent the distal end of the tube.

14. The apparatus of claim 13, further comprising means for generating a warning signal if the dimensions estimated by the estimating means are smaller than dimensions of the distal end of the tube.

15. The apparatus of claim 10, wherein the processing means includes means for determining if the tube is obstructed.

16. The apparatus of claim 15, further comprising means for generating a warning signal if the tube is obstructed by more than a predetermined percentage.

17. The apparatus of claim 10, further comprising an absorptive material coupled to an end of the generating means for substantially absorbing sound pulses moving toward the end of the generating means.

18. The apparatus of claim 10, further comprising means for displaying information generated by the processing means.

19. An apparatus for acoustically guiding placement of a distal end of an endotracheal tube within a respiratory system of a body including a trachea, a right primary bronchus, and a left primary bronchus, the apparatus comprising:
- a wave guide having a first end and a second end;
- a mechanical ventilator;
- a valve having a first inlet coupled to the first end of the wave guide and a second inlet coupled to the mechanical ventilator, the valve being movable from a first position to provide communication between the wave guide and the proximal end of the tube to a second position to provide communication between the mechanical ventilator and the proximal end of the tube;
- a speaker coupled to the wave guide for generating an incident sound pulse in the wave guide which propagates into the body when the valve is in its first position;
- a microphone coupled to the wave guide between the speaker and the first end of the wave guide for detecting sound pulses moving past the microphone in the wave guide from the incident sound pulse and reflected sound pulses from within the body; and
- means for processing the sound pulses detected by the microphone to guide proper positioning of the tube in the trachea.

20. The apparatus of claim 19, wherein the processing means includes means for providing an indication of the position of the distal end of the tube within the body.

21. The apparatus of claim 19, wherein the processing means includes means for generating a warning signal if the distal end of the tube is inserted into one of the an esophagus, the right primary bronchus, and the left primary bronchus.

22. The apparatus of claim 19, wherein the processing means includes means for estimating dimensions of the body adjacent the distal end of the tube.

23. The apparatus of claim 22, wherein the processing means includes means for generating a warning signal if the dimensions estimated by the estimating means are smaller than dimensions of the distal end of the tube.

24. The apparatus of claim 19, wherein the processing means includes means for determining if the tube is obstructed and means for generating a warning signal if the tube is obstructed by more than a predetermined percentage.

25. The apparatus of claim 19, further comprising an absorptive material coupled to the second end of the wave guide for substantially absorbing sound pulses moving toward the second end of the wave guide.

* * * * *